(12) United States Patent
Navab et al.

(10) Patent No.: US 12,419,686 B2
(45) Date of Patent: Sep. 23, 2025

(54) SPATIALLY-AWARE DISPLAYS FOR COMPUTER-ASSISTED INTERVENTIONS

(71) Applicants: Stryker Leibinger GmbH & Co. KG, Freiburg (DE); Technical University of Munich, Munich (DE)

(72) Inventors: Nassir Navab, Munich (DE); Alexander Winkler, Munich (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 1143 days.

(21) Appl. No.: 17/341,972

(22) Filed: Jun. 8, 2021

(65) Prior Publication Data

US 2021/0378750 A1  Dec. 9, 2021

Related U.S. Application Data

(60) Provisional application No. 63/036,559, filed on Jun. 9, 2020.

(51) Int. Cl.
*A61B 34/10* (2016.01)
*A61B 34/20* (2016.01)
(Continued)

(52) U.S. Cl.
CPC .............. *A61B 34/10* (2016.02); *A61B 34/20* (2016.02); *A61B 90/361* (2016.02); *A61B 90/50* (2016.02);
(Continued)

(58) Field of Classification Search
None
See application file for complete search history.

(56) References Cited

U.S. PATENT DOCUMENTS 7,493,153 B2  2/2009  Ahmed et al.
8,314,815 B2  11/2012  Navab et al.
(Continued)

FOREIGN PATENT DOCUMENTS

JP   H09154114 A   6/1997
JP   2007140977 A  6/2007
(Continued)

OTHER PUBLICATIONS

Abstract of Schnaider, M. et al., "Medarpa—A Medical Augmented Reality System for Minimal-Invasive Interventions", Studies in Health Technology and Informatics, vol. 94, 2003, pp. 312-314, 1 page.

(Continued)

*Primary Examiner* — Patricia J Park
(74) *Attorney, Agent, or Firm* — Howard & Howard Attorneys PLLC

(57) ABSTRACT

Described herein are systems, methods, and techniques for spatially-aware displays for computer-assisted interventions. A Fixed View Frustum technique renders computer images on the display using a perspective based on a virtual camera having a field-of-view facing the display and automatically updates the virtual position of the virtual camera in response to adjusting the pose of the display. A Dynamic Mirror View Frustum technique renders computer images on the display using a perspective based on a field-of-view of a virtual camera that has a virtual position behind the display device. The virtual position of the virtual camera is dynamically updated in response to movement of a user's viewpoint located in front of the display device. Slice visualization techniques are also described herein for use with the Fixed View Frustum and Dynamic Mirror View Frustum techniques.

13 Claims, 13 Drawing Sheets

(51) Int. Cl.
*A61B 90/00* (2016.01)
*A61B 90/50* (2016.01)
*G02B 27/00* (2006.01)
*G02B 27/01* (2006.01)

(52) U.S. Cl.
CPC ..... *G02B 27/0093* (2013.01); *G02B 27/0179* (2013.01); *A61B 2034/102* (2016.02); *A61B 2034/105* (2016.02); *A61B 2034/2057* (2016.02); *A61B 2034/2065* (2016.02); *A61B 2090/365* (2016.02); *A61B 2090/502* (2016.02); *G02B 2027/0187* (2013.01)

(56) References Cited

U.S. PATENT DOCUMENTS

| | | | |
|---|---|---|---|
| 8,782,565 | B2 | 7/2014 | Fretwell et al. |
| 8,808,164 | B2 | 8/2014 | Hoffman et al. |
| 9,008,757 | B2 | 4/2015 | Wu |
| 9,119,655 | B2 | 9/2015 | Bowling et al. |
| 9,251,721 | B2 | 2/2016 | Lampotang et al. |
| 9,532,848 | B2 | 1/2017 | Amiot et al. |
| 9,707,043 | B2 | 7/2017 | Bozung |
| 10,646,283 | B2 | 5/2020 | Johnson et al. |
| 10,646,285 | B2 | 5/2020 | Siemionow et al. |
| 11,050,990 | B2 | 6/2021 | Casas |
| 11,382,712 | B2 | 7/2022 | Elimelech et al. |
| 2001/0036245 | A1 | 11/2001 | Kienzle et al. |
| 2007/0038944 | A1 | 2/2007 | Carignano et al. |
| 2007/0073137 | A1 | 3/2007 | Schoenefeld |
| 2008/0158340 | A1 | 7/2008 | Shibata et al. |
| 2009/0248036 | A1 | 10/2009 | Hoffman et al. |
| 2010/0149213 | A1 | 6/2010 | Navab et al. |
| 2010/0210902 | A1 | 8/2010 | Navab et al. |
| 2012/0330429 | A1 | 12/2012 | Axelson, Jr. et al. |
| 2013/0096575 | A1 | 4/2013 | Olson |
| 2014/0276949 | A1 | 9/2014 | Staunton et al. |
| 2014/0323803 | A1 | 10/2014 | Hoffman et al. |
| 2015/0025549 | A1 | 1/2015 | Kilroy et al. |
| 2016/0357578 | A1 | 12/2016 | Kim et al. |
| 2018/0028054 | A1 | 2/2018 | Hoffman et al. |
| 2018/0161008 | A1* | 6/2018 | Huepf ............... G06T 11/60 |
| 2018/0185113 | A1* | 7/2018 | Gregerson ............ A61B 34/35 |
| 2020/0054412 | A1 | 2/2020 | Fuerst et al. |
| 2020/0163723 | A1 | 5/2020 | Wolf et al. |
| 2021/0104063 | A1* | 4/2021 | Kassis ................. G06F 3/0304 |

FOREIGN PATENT DOCUMENTS

| | | |
|---|---|---|
| JP | 2008140271 A | 6/2008 |
| WO | 2020036611 A1 | 2/2020 |
| WO | 2020084625 A1 | 4/2020 |
| WO | 2020113030 A1 | 6/2020 |
| WO | 2021014211 A1 | 1/2021 |

OTHER PUBLICATIONS

Bichlmeier, C. et al., "The Virtual Mirror: A New Interaction Paradigm for Augmented Reality Environments", IEEE Transactions on Medical Imaging, vol. 28, No. 9, Sep. 2009, pp. 1498-1510.

Blackwell, M. et al., "An Image Overlay System for Medical Data Visualization", Medical Image Analysis, vol. 4, No. 1, Mar. 2000, pp. 67-72.

Blum, Tobias et al., "Miracle: An Augmented Reality Magic Mirror System for Anatomy Education", IEEE Virtual Reality, Orange County, CA, Mar. 4-8, 2012, 3 pages.

Fatouhi, Javad et al., "Reflective-AR Display: An Interaction Methodology for Virtual-To-Real Alignment in Medical Robotics", IEEE Robotics and Automation Letters, Jan. 2020, 8 pages.

Fatouhi, Javad et al., "Spatiotemporal-Aware Augmented Reality: Redefining HCI in Image-guided Therapy", Journal of Class Files, Mar. 2020, 10 pages.

Goebbels, G., et al., "Development of an Augmented Reality System for Intra-Operative Navigation in Maxillo-Facial Surgery", Proceedings of AR/VR-Statustagung, Leipzig, 2004, 8 pages.

Houston, E.J., "Elementary Electricity, Chapter 13: The X-Rays", Popular Electricity Magazine, vol. 2, 1908, 6 pages.

Kooima, Robert, "Generalized Perspective Projection", 2008-2013, https://csc.lsu.edu/kooima/articles/genperpective/index.html, 8 pages.

Navab, Nassir et al., "Laparoscopic Virtual Mirror: New Interaction Paradigm for Monitor Based Augmented Reality", IEEE Virtual Reality Conference, Charlotte, NC, Mar. 10-14, 2007, 8 pages.

Park, J.S. et al., "Visible Korean Human: Improved Serially Sectioned Images of the Entire Body", IEEE Transactions on Medical Imaging, vol. 24, No. 3, March 005, pp. 352-360.

Sielhorst, Tobia, "New Methods for Medical Augmented Reality Dissertation", Computer-Aided Medical Procedures, https://mediatum.ub.tum.de/doc/647399/647399.pdf, Oct. 25, 2007, 147 pages.

Tuceryan, M. et al., "Calibration Requirements and Procedures for a Monitor-Based Augmented Reality System", IEEE Transactions on Visualization and Computer Graphics, vol. 1, No. 3, Sep. 1995, pp. 255-273.

Vogt, Sebastian, "Real-Time Augmented Reality for Image-Guided Interventions", 2009, 211 pages.

Weber, S. et al., "The Navigated Image Viewer Evaluation in Maxillofacial Surgery", In: Ellis, R.E et al., Medical Image Computing and Computer-Assisted Intervention—MICCAI, Lecture Notes in Computer Science, Springer, Berlin,2003, pp. 762-769.

Wilkinson, E.P. et al, "Remote-Rendered 3D CT Angiography (3DCTA) as Intraoperative Aid in Cerebrovascular Neurosurgery", Computer Aided Suegery, vol. 4, No. 5, 1999, pp. 256-263.

Winkler, Alexander, "New Augmented Reality Setup Presentation", Mar. 12, 2020, 18 pages.

International Search Report for Application No. PCT/IB2021/055047 dated Oct. 19, 2021, 2 pages.

English language abstract and machine-assisted English translation for JPH 09-154114 A extracted from espacenet.com database on Dec. 20, 2024, 7 pages.

English language abstract and machine-assisted English translation for JP 2007-140977 A extracted from espacenet.om database on Dec. 20, 2024, 18 pages.

English language abstract for JP 2008-140271 A extracted from espacenet.com database on Dec. 20, 2024, 1 page.

* cited by examiner

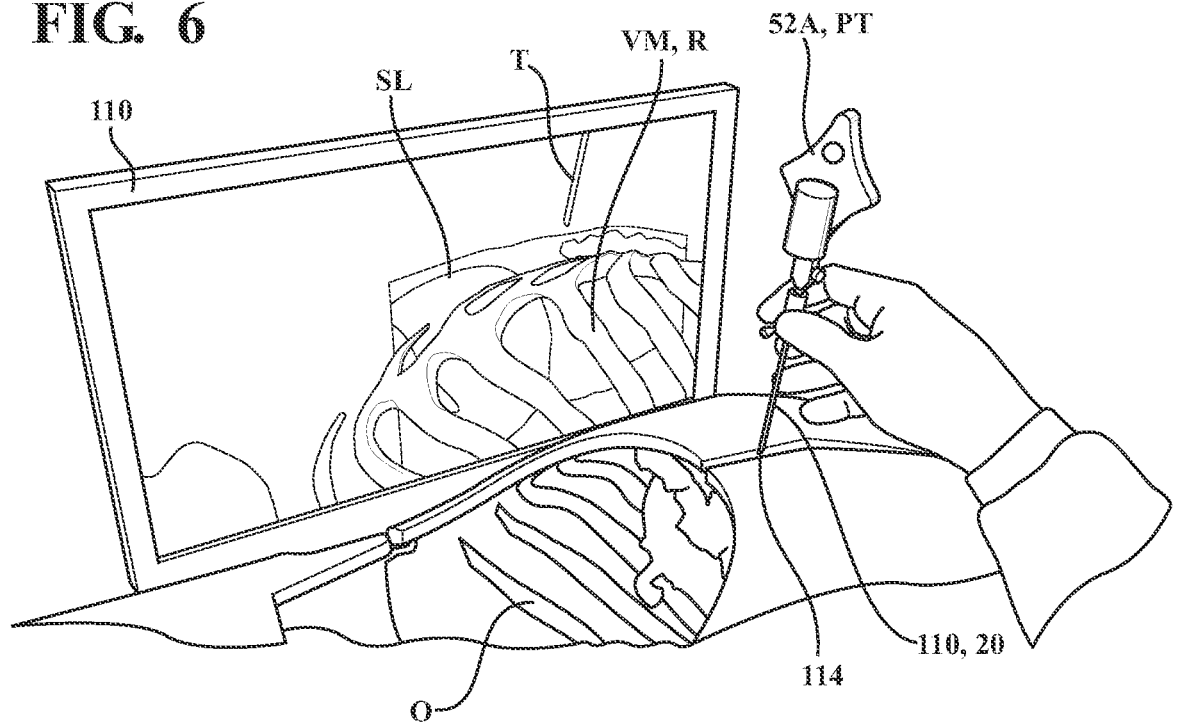

SPATIALLY-AWARE DISPLAYS FOR COMPUTER-ASSISTED INTERVENTIONS

CROSS-REFERENCE TO RELATED APPLICATIONS

The subject United States Non-Provisional Patent application claims priority to U.S. Provisional Patent Application No. 63/036,559, filed Jun. 9, 2020, the entire contents of which are hereby incorporated by reference.

BACKGROUND

In the very early days of X-ray fluoroscopy, radiologists used fluorescent handheld screens which were placed into the beam emanating from the X-ray source passing through the patient. The image had a direct correlation to the X-ray source, the patient, the screen and the observer, as it was observed directly where it was produced. With advances in imaging and display technology, it became possible to view static or live images of the patient anatomy at any location, where a monitor could be positioned. This had the advantage of more practical patient and display positioning and reduced dose to the interventionalist, but the intuitive perception of the spatial configuration between X-ray source, patient, screen, and the viewer was lost.

CT or MRI scans, which are inherently 3D, are often visualized as a set of three orthogonal slices along the anatomical axes of the patient or along the axis of an instrument. Only recently have 3D images been rendered on displays in operating rooms, often in addition to the slice visualizations. These are often volume renderings from viewpoints, which can be defined and controlled by the user. Many surgeons prefer 2D images rather than 3D graphic renderings as they have been well trained in interpreting them and thus this defines the current clinical standard.

Navigation in surgery has been introduced since the early 1990s and takes advantage of different visualization techniques. Many systems show slices of pre- or intra-operative data with additional annotations. These annotations relate to a surgical plan, which needs to be carried out in surgery. Such annotations are often an attempt to visualize deep seated anatomical targets and safe paths for the surgeon to reach them based on pre-operative images. In such systems, when rendering images, the position of the surgeon and location of displays are not taken into consideration. The position of the display therefore does not affect the visualization nor does the position of observer.

A series of related work is often referred to as Augmented Reality windows (AR-windows). Prior techniques tracked semi-transparent display for medical in-situ augmentation, which incorporated a head tracker and stereo glasses. Such semi-transparent displays included a half-silvered glass pane, which reflected the image from a computer display. Others have addressed the same problem of creating an AR-window on patient anatomy using a semi-transparent display between the patient and the surgeon. However, such prior techniques replaced the half-silvered glass pane with an active matrix LCD. Later attempts approached the problem again with a half-silvered glass pane, which rejected the projection of two DLP projectors generating high contrast images. Other systems comprised of a tracked mobile opaque screen in which the position of the screen affected the visualization. Once again, such prior systems were placed between the surgeon and the patient showing a slice view of the anatomy. However, in this system, the user's perspective is not considered, i.e., the image on the screen is merely two-dimensional, independent from the viewpoint of the surgeon.

Others have presented an AR visualization inspired by the dentists' approach for examining the patient's mouth without changing their viewpoints. Such techniques identified that in some AR applications, rotating the object or moving around it is impossible. It was suggested to generate additional virtual mirroring views to offer secondary perspectives on virtual objects within an AR view. Spatially tracked joysticks were utilized to move a virtual mirror which reflected the virtual data like a real mirror within the AR view of a head mounted device (HMD).

SUMMARY

This Summary introduces a selection of concepts in a simplified form that are further described below in the Detailed Description below. This Summary is not intended to limit the scope of the claimed subject matter and does not necessarily identify each and every key or essential feature of the claimed subject matter.

In a first aspect, a system for aiding in interaction with a physical object is provided, the system comprising: a display device defining a plane and being located on a first side of the physical object; and a navigation system coupled to a control system and being configured to: register computer images to the physical object; track a pose of the physical object and the display device in a common coordinate system; and control the display device to render the registered computer images according to the tracked pose of the physical object and the display device; and wherein a perspective of the rendering is based on a virtual camera that has a virtual position located on a second side of the physical object opposite to the first side, and wherein the virtual camera has a field-of-view that faces the plane of display device, and wherein the virtual position of the virtual camera updates automatically in response to adjustment to the pose of the display device.

In a second aspect, a navigation system of the system of the first aspect is provided.

In a third aspect, a non-transitory computer readable medium or computer program product are provided comprising instructions, which when executed by one or more processors, are configured to implement the control system of the first aspect.

In a fourth aspect, a method of operating a system for aiding in interaction with a physical object is provided, the system comprising: a display device defining a plane and being located on a first side of the physical object; and a navigation system coupled to a control system, the method comprising: registering computer images to the physical object; tracking a pose of the physical object and the display device in a common coordinate system; and controlling the display device to render the registered computer images according to the tracked pose of the physical object and the display device; and wherein a perspective of the rendering is based on a virtual camera having a virtual position located on a second side of the physical object opposite to the first side, and wherein the virtual camera has a field-of-view facing the plane of display device, and automatically updating the virtual position of the virtual camera in response to adjusting the pose of the display device.

In a fifth aspect, a non-transitory computer readable medium or computer program product are provided comprising instructions, which when executed by one or more processors, are configured to implement the method of the fourth aspect.

In a sixth aspect, a system for aiding in interaction with a physical object is provided, the system comprising: a display device defining a plane, wherein the physical object is located in front of the plane; a navigation system coupled to a control system and being configured to: register computer images to the physical object; track a pose of the physical object, the display device, and a user's viewpoint in a common coordinate system; and control the display device for rendering the registered computer images according to the tracked pose of the physical object, the display device, and the user's viewpoint; and wherein a perspective of the rendering is based on a field-of-view of a virtual camera that has a virtual position behind the plane, and wherein the virtual position of the virtual camera is automatically updated in response to movement of the tracked pose of the user's viewpoint.

In a seventh aspect, a navigation system of the system of the sixth aspect is provided.

In an eighth aspect, a non-transitory computer readable medium or computer program product are provided comprising instructions, which when executed by one or more processors, are configured to implement the control system of the sixth aspect.

In a ninth aspect, a method of operating a system for aiding in interaction with a physical object is provided, the system comprising a display device defining a plane, wherein the physical object is located in front of the plane, and a navigation system coupled to a control system, the method comprising: registering computer images to the physical object; tracking a pose of the physical object, the display device, and a user's viewpoint in a common coordinate system; and controlling the display device for rendering the registered computer images according to the tracked pose of the physical object, the display device, and the user's viewpoint; and wherein a perspective of the rendering is based on a field-of-view of a virtual camera having a virtual position behind the plane, and automatically updating the virtual position of the virtual camera in response to movement of the tracked pose of the user's viewpoint.

In a tenth aspect, a non-transitory computer readable medium or computer program product are provided comprising instructions, which when executed by one or more processors, are configured to implement the method of the ninth aspect.

BRIEF DESCRIPTION OF THE DRAWINGS

FIG. 6 is an illustrative real-world example of one implementation of the Screen Parallel Slice Visualization technique wherein the slice is displayed relative to the 3D model of the physical object (e.g., patient) depending on the pose of a tracked tool.

FIG. 7 is an illustrative real-world example of one implementation of the Screen Parallel Slice Visualization technique wherein the displayed images are modified to account for the spatial layering of the object, tool, and slice relative to one other so as to mimic the actual spatial location of the same in the real coordinate system in which these items exist.

DETAILED DESCRIPTION

I. Surgical System Overview

Figure 1:
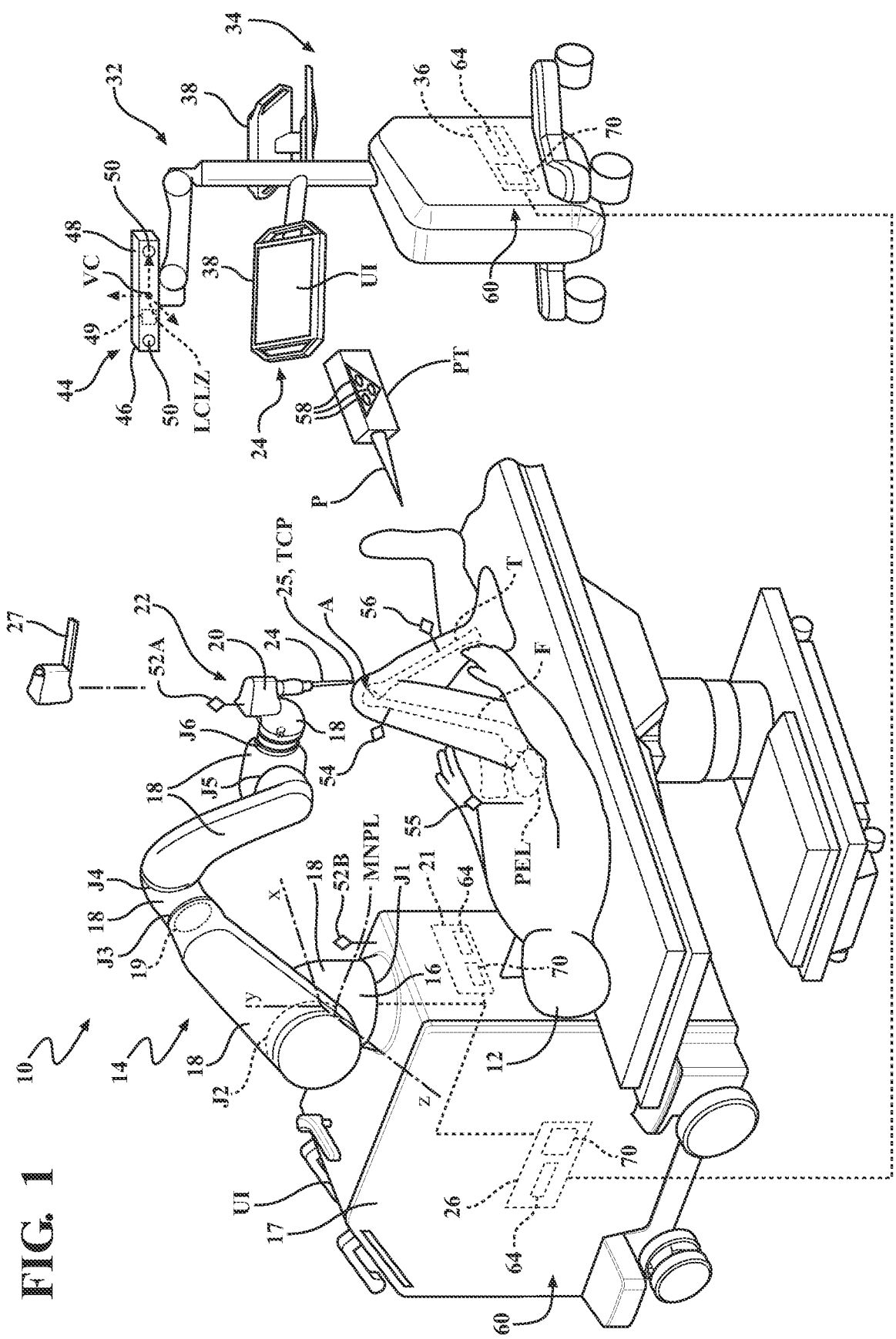
FIG. 1 illustrates an example of a surgical system that can be utilized with the spatially-aware display techniques described herein.
Figure 2:
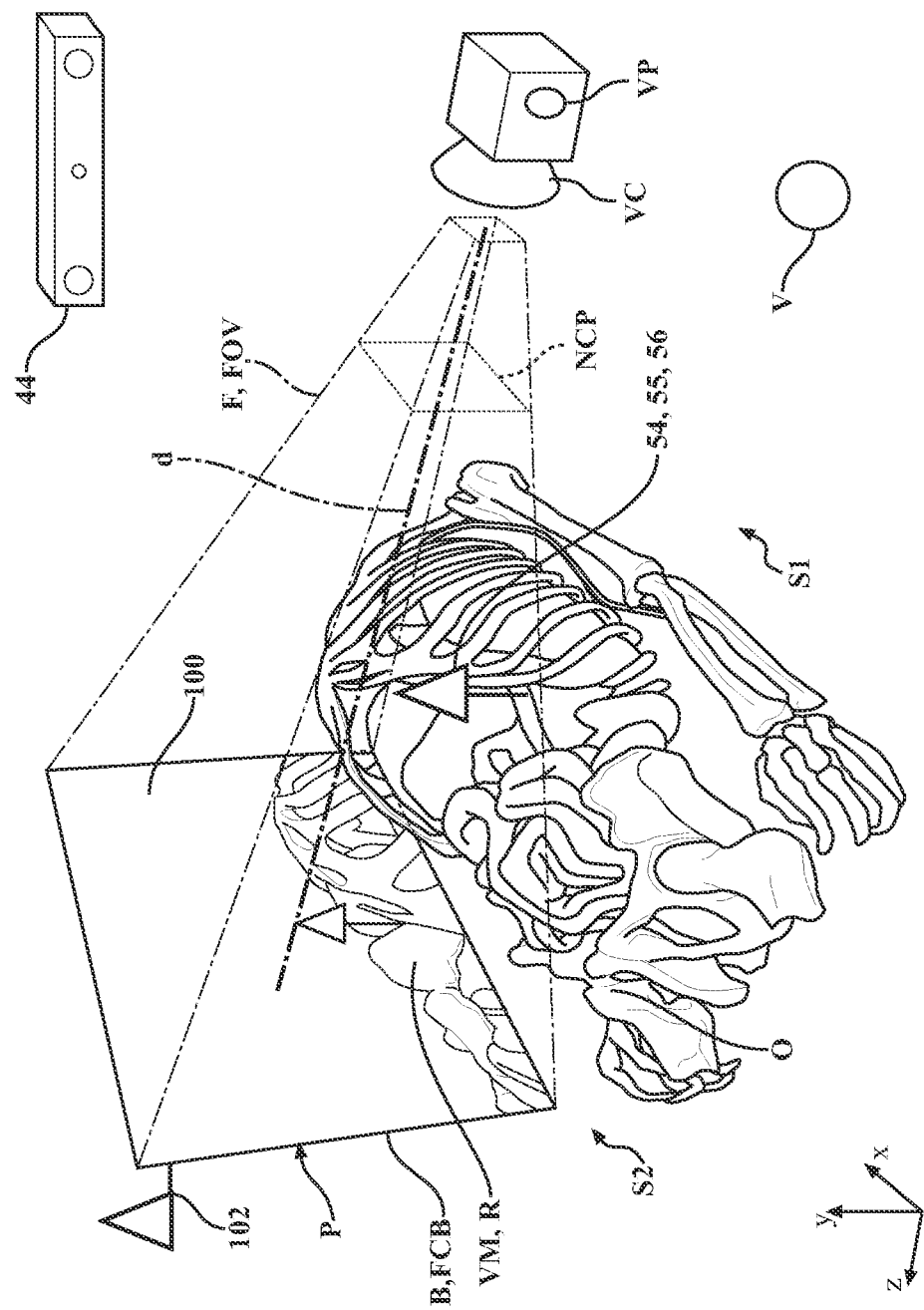
FIG. 2 is a simulated illustration of one implementation and setup of a Fixed View Frustum visualization technique wherein the perspective of the images displayed depend on the pose of the display device and pose of the physical object (e.g., patient) relative to the display device.

Referring to FIG. 1, a surgical system 10 is illustrated which can be utilized with the spatially-aware displays described in Section II below. The system 10 is useful for treating a target site or anatomical volume A of a patient 12, such as treating bone or soft tissue. In FIG. 1, the patient 12 is undergoing a surgical procedure. The anatomy in FIG. 1 includes a femur F, pelvis PEL, and a tibia T of the patient 12. The surgical procedure may involve tissue removal or other forms of treatment. Treatment may include cutting, coagulating, lesioning the tissue, other in-situ tissue treatments, or the like. In some examples, the surgical procedure involves partial or total knee or hip replacement surgery, shoulder replacement surgery, spine surgery, or ankle surgery. In some examples, the system 10 is designed to cut away material to be replaced by surgical implants, such as hip and knee implants, including unicompartmental, bicompartmental, multicompartmental, or total knee implants, acetabular cup implants, femur stem implants, screws, anchors, other fasteners, and the like. Some of these types of implants are shown in U.S. Patent Application Publication No. 2012/0330429, entitled, "Prosthetic Implant and Method of Implantation," the disclosure of which is hereby incorporated by reference. The system 10 and techniques disclosed herein may be used to perform other procedures, surgical or non-surgical, or may be used in industrial applications or other applications.

The system 10 may include a robotic manipulator 14, also referred to as a surgical robot. The manipulator 14 has a base 16 and plurality of links 18. A manipulator cart 17 supports the manipulator 14 such that the manipulator 14 is fixed to the manipulator cart 17. The links 18 collectively form one or more arms of the manipulator 14 (e.g., robotic arms). The manipulator 14 may have a serial arm configuration (as shown in FIG. 1), a parallel arm configuration, or any other suitable manipulator configuration. In other examples, more than one manipulator 14 may be utilized in a multiple arm configuration.

In the example shown in FIG. 1, the manipulator 14 comprises a plurality of joints J and a plurality of joint encoders 19 located at the joints J for determining position data of the joints J. For simplicity, only one joint encoder 19 is illustrated in FIG. 1, although other joint encoders 19 may be similarly illustrated. The manipulator 14 according to one example has six joints J1-J6 implementing at least six-degrees of freedom (DOF) for the manipulator 14. However, the manipulator 14 may have any number of degrees of freedom and may have any suitable number of joints J and may have redundant joints.

The manipulator 14 need not require joint encoders 19 but may alternatively, or additionally, utilize motor encoders present on motors at more than one or each joint J. Also, the manipulator 14 need not require rotary joints, but may alternatively, or additionally, utilize one or more prismatic joints. Any suitable combination of joint types is contemplated.

The base 16 of the manipulator 14 is generally a portion of the manipulator 14 that provides a fixed reference coordinate system for other components of the manipulator 14 or the system 10 in general. Generally, the origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the cart 17. In one example, the base 16 is defined at an intersection of the axes of joints J1 and J2. Thus, although joints J1 and J2 are moving components in reality, the intersection of the axes of joints J1 and J2 is nevertheless a virtual fixed reference pose, which provides both a fixed position and orientation reference and which does not move relative to the manipulator 14 and/or manipulator cart 17.

In some examples, the manipulator 14 can be a hand-held manipulator where the base 16 is a base portion of a tool (e.g., a portion held free-hand by the user) and the tool tip is movable relative to the base portion. The base portion has a reference coordinate system that is tracked and the tool tip has a tool tip coordinate system that is computed relative to the reference coordinate system (e.g., via motor and/or joint encoders and forward kinematic calculations). Movement of the tool tip can be controlled to follow the path since its pose relative to the path can be determined. Such a manipulator 14 is shown in U.S. Pat. No. 9,707,043, filed on Aug. 31, 2012, entitled, "Surgical Instrument Including Housing, A Cutting Accessory that Extends from the Housing and Actuators that Establish the Position of the Cutting Accessory Relative to the Housing," which is hereby incorporated herein by reference.

The manipulator 14 and/or manipulator cart 17 house a manipulator controller 26, or other type of control unit. The manipulator controller 26 may comprise one or more computers, or any other suitable form of controller that directs the motion of the manipulator 14. The manipulator controller 26 may have a central processing unit (CPU) and/or other processors, memory (not shown), and storage (not shown). The manipulator controller 26 is loaded with software as described below. The processors could include one or more processors to control operation of the manipulator 14. The processors can be any type of microprocessor, multi-processor, and/or multi-core processing system. The manipulator controller 26 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any implementation to a single processor. The manipulator 14 may also comprise a user interface UI with one or more displays and/or input devices (e.g., push buttons, sensors, switches, keyboard, mouse, microphone (voice-activation), gesture control devices, touchscreens, joysticks, foot pedals, etc.).

A surgical tool 20 couples to the manipulator 14 and is movable relative to the base 16 to interact with the anatomy in certain modes. The tool 20 is or forms part of an end effector 22 supported by the manipulator 14 in certain embodiments. The tool 20 may be grasped by the user. One possible arrangement of the manipulator 14 and the tool 20 is described in U.S. Pat. No. 9,119,655, filed on Aug. 2, 2013, entitled, "Surgical Manipulator Capable of Controlling a Surgical Instrument in Multiple Modes," the disclosure of which is hereby incorporated by reference. The manipulator 14 and the tool 20 may be arranged in alternative configurations. The tool 20 can be like that shown in U.S. Patent Application Publication No. 2014/0276949, filed on Mar. 15, 2014, entitled, "End Effector of a Surgical Robotic Manipulator," hereby incorporated by reference. Separate hand-held surgical tools can be utilized in addition to or alternative to the manipulator 14 and tool 20.

The tool 20 includes an energy applicator 24 designed to contact the tissue of the patient 12 at the target site. In one example, the energy applicator 24 is a bur 25. The bur 25 may be spherical and comprise a spherical center, radius (r) and diameter. Alternatively, the energy applicator 24 may be a drill bit, a saw blade 27 (see alternative tool in FIG. 1), an ultrasonic vibrating tip, or the like. The tool 20 and/or energy applicator 24 may comprise any geometric feature, e.g., perimeter, circumference, radius, diameter, width, length, volume, area, surface/plane, range of motion envelope (along any one or more axes), etc. The geometric feature may be considered to determine how to locate the tool 20 relative to the tissue at the target site to perform the desired treatment. In some of the embodiments described herein, a spherical bur having a tool center point (TCP) and a sagittal saw blade having a TCP will be described for convenience and ease of illustration, but is not intended to limit the tool 20 to any particular form.

The tool 20 may comprise a tool controller 21 to control operation of the tool 20, such as to control power to the tool 20 (e.g., to a tool drive such as a rotary motor of the tool 20), control movement of the tool 20, control irrigation/aspiration of the tool 20, and/or the like. The tool controller 21 may be in communication with the manipulator controller 26 or other components. The tool 20 may also comprise a user interface UI with one or more displays and/or input devices (e.g., push buttons, triggers, sensors, switches, keyboard, mouse, microphone (voice-activation), gesture control devices, touchscreens, joysticks, foot pedals, etc.) that are coupled to the tool controller 21, manipulator controller 26, and/or other controllers described herein. The manipulator controller 26 controls a state (e.g., position and/or orientation) of the tool 20 (e.g., of the TCP) with respect to a coordinate system, such as the manipulator coordinate system MNPL. The manipulator controller 26 can control velocity (linear or angular), acceleration, or other derivatives of motion of the tool 20.

The tool center point (TCP), in one example, is a predetermined reference point defined at the energy applicator 24. The TCP has a known, or able to be calculated (i.e., not necessarily static), pose relative to other coordinate systems. The geometry of the energy applicator 24 is known in or defined relative to a TCP coordinate system. The TCP may be located at the spherical center of the bur 25 of the tool 20 or at the distal end of the saw blade 27 such that only one point is tracked. The TCP may be defined in various ways depending on the configuration of the energy applicator 24. The manipulator 14 could employ the joint/motor encoders, or any other non-encoder position sensing method, to enable a pose of the TCP to be determined. The manipulator 14 may use joint measurements to determine TCP pose and/or could employ techniques to measure TCP pose directly. The control of the tool 20 is not limited to a center point. For example, any suitable primitives, meshes, etc., can be used to represent the tool 20.

The system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 tracks movement of various objects. Such objects include, for example, the manipulator 14, the tool 20 and the anatomy, e.g., femur F, pelvis PEL, and tibia T. The navigation system 32 tracks these objects to gather state information of the objects with respect to a (navigation) localizer coordinate system LCLZ. Coordinates in the localizer coordinate system LCLZ may be transformed to the manipulator coordinate system MNPL, to other coordinate systems, and/or vice-versa, using transformations.

The navigation system 32 may include a cart assembly 34 that houses a navigation controller 36, and/or other types of control units. A navigation user interface UI is in operative communication with the navigation controller 36. The navigation user interface includes one or more displays 38. The navigation system 32 is capable of displaying a graphical representation of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, a keyboard, a mouse, a microphone (voice-activation), gesture control devices, foot pedals, and the like.

The navigation system 32 also includes a navigation localizer 44 coupled to the navigation controller 36. In one example, the localizer 44 is an optical localizer and includes a camera unit 46. The camera unit 46 has an outer casing 48 that houses one or more optical sensors 50. The localizer 44 may comprise its own localizer controller 49 and may further comprise a video camera VC.

The navigation system 32 includes one or more trackers. In one example, the trackers include a pointer tracker PT, one or more manipulator trackers 52A, 52B, a first patient tracker 54, a second patient tracker 55, and a third patient tracker 56. In the illustrated example of FIG. 1, the manipulator tracker is firmly attached to the tool 20 (i.e., tracker 52A), the first patient tracker 54 is firmly affixed to the femur F of the patient 12, the second patient tracker 55 is firmly affixed to the pelvis PEL of the patient 12, and the third patient tracker 56 is firmly affixed to the tibia T of the patient 12. In this example, the patient trackers 54, 55, 56 are firmly affixed to sections of bone. The pointer tracker PT is firmly affixed to a pointer P used for registering the anatomy to the localizer coordinate system LCLZ. The manipulator tracker 52A, 52B may be affixed to any suitable component of the manipulator 14, in addition to, or other than the tool 20, such as the base 16 (i.e., tracker 52B), or any one or more links 18 of the manipulator 14. The trackers 52A, 52B, 54, 55, 56, PT may be fixed to their respective components in any suitable manner. For example, the trackers may be rigidly fixed, flexibly connected (optical fiber), or physically spaced (e.g., ultrasound), as long as there is a suitable (supplemental) way to determine the relationship (measurement) of that respective tracker to the object with which it is associated.

Any one or more of the trackers may include active markers 58. The active markers 58 may include light emitting diodes (LEDs). Alternatively, the trackers 52A, 52B, 54, 55, 56, PT may have passive markers, such as reflectors, which reflect light emitted from the camera unit 46. Other suitable markers not specifically described herein may be utilized.

The localizer 44 tracks the trackers 52A, 52B, 54, 55, 56, PT to determine a state of the trackers 52A, 52B, 54, 55, 56, PT, which correspond respectively to the state of the object respectively attached thereto. The localizer 44 may perform known triangulation techniques to determine the states of the trackers 52, 54, 55, 56, PT, and associated objects. The localizer 44 provides the state of the trackers 52A, 52B, 54, 55, 56, PT to the navigation controller 36. In one example, the navigation controller 36 determines and communicates the state of the trackers 52A, 52B, 54, 55, 56, PT to the manipulator controller 26. As used herein, the state of an object includes, but is not limited to, data that defines the position and/or orientation of the tracked object or equivalents/derivatives of the position and/or orientation. For example, the state may be a pose of the object, and may include linear velocity data, and/or angular velocity data, and the like.

The navigation controller 36 may comprise one or more computers, or any other suitable form of controller. Navigation controller 36 has a central processing unit (CPU) and/or other processors, memory (not shown), and storage (not shown). The processors can be any type of processor, microprocessor or multi-processor system. The navigation controller 36 is loaded with software. The software, for example, converts the signals received from the localizer 44 into data representative of the position and orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any implementation to a single processor.

Although one example of the navigation system 32 is shown that employs triangulation techniques to determine object states, the navigation system 32 may have any other suitable configuration for tracking the manipulator 14, tool 20, and/or the patient 12. In another example, the navigation system 32 and/or localizer 44 are ultrasound-based. For example, the navigation system 32 may comprise an ultrasound imaging device coupled to the navigation controller 36. The ultrasound imaging device images any of the aforementioned objects, e.g., the manipulator 14, the tool 20, and/or the patient 12, and generates state signals to the navigation controller 36 based on the ultrasound images. The ultrasound images may be 2-D, 3-D, or a combination of both. The navigation controller 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation controller 36. The manipulator 14, the tool 20, and/or the patient 12 may comprise RF emitters or transponders attached thereto. The RF emitters or transponders may be passive or actively energized. The RF transceiver transmits an RF tracking signal and generates state signals to the navigation controller 36 based on RF signals received from the RF emitters. The navigation controller 36 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52A, 52B, 54, 55, 56, PT shown in FIG. 1.

In yet another example, the navigation system 32 and/or localizer 44 are electromagnetically based. For example, the navigation system 32 may comprise an EM transceiver coupled to the navigation controller 36. The manipulator 14, the tool 20, and/or the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the navigation controller 36 based upon EM signals received from the trackers. The navigation controller 36 may analyze the received EM signals to associate relative states thereto. Again, such navigation system 32 examples may have structural configurations that are different than the navigation system 32 configuration shown in FIG. 1.

The navigation system 32 may have any other suitable components or structure not specifically recited herein. Furthermore, any of the techniques, methods, and/or components described above with respect to the navigation system 32 shown may be implemented or provided for any of the other examples of the navigation system 32 described herein. For example, the navigation system 32 may utilize solely inertial tracking or any combination of tracking techniques, and may additionally or alternatively comprise, fiber optic-based tracking, machine-vision tracking, and the like. While in our certain implementation, optical IR tracking is utilized, the concepts and techniques described herein may be utilized to work with any sufficiently accurate 6D tracking technology. Furthermore, we assume that existing surgical navigation systems already contain appropriate methods for registering pre-operative image data and surgical plans to the patient before surgery.

The system 10 includes a control system 60 that comprises, among other components, any one or more of the manipulator controller 26, the navigation controller 36, and the tool controller 21. The control system 60 includes one or more software programs and software modules. The software modules may be part of the program or programs that operate on the manipulator controller 26, navigation controller 36, tool controller 21, or any combination thereof, to process data to assist with control of the system 10. The software programs and/or modules include computer readable instructions stored in non-transitory memory 64 on the manipulator controller 26, navigation controller 36, tool controller 21, or a combination thereof, to be executed by one or more processors 70 of the controllers 21, 26, 36. The memory 64 may be any suitable configuration of memory, such as RAM, non-volatile memory, etc., and may be implemented locally or from a remote database. Additionally, software modules for prompting and/or communicating with the user may form part of the program or programs and may include instructions stored in memory 64 on the manipulator controller 26, navigation controller 36, tool controller 21, or any combination thereof. The user may interact with any of the input devices of the navigation user interface UI or other user interface UI to communicate with the software modules. The user interface software may run on a separate device from the manipulator controller 26, navigation controller 36, and/or tool controller 21.

The control system 60 may comprise any suitable configuration of input, output, and processing devices suitable for carrying out the functions and methods described herein. The control system 60 may comprise the manipulator controller 26, the navigation controller 36, or the tool controller 21, or any combination thereof, or may comprise only one of these controllers. These controllers may communicate via a wired bus or communication network, via wireless communication, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

II. Spatially-Aware Display Techniques

Described herein are systems, methods, and techniques related to spatially-aware displays for computer assisted interventions. A novel display and visual interaction paradigm is presented, which aims at reducing the complexity of understanding the spatial transformations between the user's (e.g., surgeon) viewpoint, a physical object (e.g., a patient), 2D and 3D data (e.g., the pre/intra-operative patient data), and tools during computer-assisted interventions. The interventional display, for example in surgical navigation systems, can be registered both to the patient and to the surgeon's view. With this technique, the surgeon can keep his/her own direct view to the patient independent of any need for additional display or direct view augmentation. In some implementations, the monitor used in the operating room is registered to the patient and surgeon's viewpoint. This enables the physicians to effortlessly relate their view of tools and patient to the virtual representation of the patient data. The direct view of the surgeon onto the patient and his/her working space can remain unchanged. The position and orientation of the display plays an integral part of the visualization pipeline. Therefore, the pose of the display is dynamically tracked relative to other objects of interest, such as the patient, instruments, and in some implementations, the surgeon's head. This information is then used as an input to the image-guided surgery visualization user interface.

At least two implementations are presented. The first one uses a "Fixed View Frustum" relating the pose of the display to the patient and tools. For the Fixed View Frustum technique, the display is tracked for example by attaching a tracking marker and calibrating the spatial relation between the physical display and the tracking marker.

The second one is built upon the mirror metaphor and extends the first technique to also integrate the pose of the surgeon's head as an additional parameter within the visualization pipeline, in which case the display will be associated to a "Dynamic Mirror View Frustum". The surgeon's viewpoint is tracked for visualization techniques for the Dynamic Mirror View Frustum. Estimation of the surgeon's viewpoint can be achieved either by using a head tracking target or by mounting a camera to the surgical display in combination with existing video-based head-pose estimation algorithms. Once the tracking information is available in a common global co-ordinate system, we can compute the spatial relationship between the patient, the surgical display, the tools and the surgeon's viewpoint by deriving the relevant transformations from the spatial relations of the tracked entities.

These novel display and visual exploration paradigms aim at reducing the complexity of understanding spatial transformations between a user's viewpoint, the physical object (O), the pre/intra-operative 2D and 3D data, and surgical tools 110, 20 during computer assisted interventions with minimal change in the current setups. Any surgical tracking system can be used to track the display, tool and user's head supporting the integration into computer assisted intervention systems. The solutions presented allow physicians to effortlessly relate their view of tools and the patient to the virtual data on surgical monitors. The users gain the possibility of interacting with the patient data just by intuitively moving their viewing position and observing it from a different perspective in relation to the patient position independent from the need for an interaction device like a mouse or joystick.

A. Fixed View Frustum Visualization Technique

With reference to FIGS. 2-8, one example visualization method that can be utilized with the surgical system 10 comprises a Fixed View Frustum (FVF) for aiding in user interaction with a physical object (O). The physical object (O) can be a physical anatomy, as shown in the Figures, or any other object requiring interaction, setup, or intervention, such as a surgical device, robotic device, surgical training model of an anatomy, and the like. For simplicity, the physical anatomy is shown as the object, however, the concept is not limited to such.

One or more external screen(s) or display device(s) 100 are provided. These display devices 100 can be those displays 38 on the navigation cart 34 assembly or any other external display that is spaced apart from and not worn by the user. The display device 100 can be any suitable type of display, including, but not limited to: LED, LCD, OLED, touchscreen, holographic; and can display any type of imagery. The display device 100 can also take any suitable geometric shape, including rectangular, square, circular, or the like.

During use, the display device(s) 100 is located on a side (S2) of the physical object (O) opposite to a side (S1) where the user is located. In other words, the physical object (O) is between a user's viewpoint (V) and the display device 100. Hence, the display device 100 utilized herein is distinguished from head-mounted displays or tablet screens that are between the user's viewpoint (V) and the object (O). Here, the physical object (O) is shown as a virtual representation merely for illustrative purposes.

Of course, the user is not prohibited from moving between the physical object (O) and the display device 100. However, implementation of the spatially-aware display takes into account the practical reality that a surgeon desires to visualize the physical object (O) on the side which he/she is presently located and that typically the side of the physical object (O) that is opposite to the surgeon would provide an inverted perspective. This will be understood further below in context of the field of view of the virtual camera which forward-faces the display device 100.

The display device 100 defines a plane (P). The plane (P) is defined parallel to or coincident with the actual front face of the display device 100. Here, the plane (P) is a virtual object utilized for computational purposes, as will be described below. The control system 60, which includes the navigation system 32 comprising any one or more controllers described herein, is configured to register computer images (R) to the physical object (O). Registration of the physical object (O) is not limited to any technique and can occur according to any suitable method including digitization of the physical object (O), touchless registration (e.g., ultrasonic), 2D/3D image registration utilizing an imaging device (e.g., CT, X-Ray), or the like. The computer images (R) can be represented as a virtual model (VM) of any portions of the physical object (O). These computer images (R) can be rendered on the display device 100. These computer images (R) can be static or dynamic and can include actual/real video graphic images, mixed reality, augmented reality, virtual reality images or models, or any combination thereof.

The control system 60, by way of the localizer 44 tracks a pose of the physical object (O) utilizing any of the patient tracking techniques described above, including but not limited to the patient trackers 54, 55, 56. In some implementations, the localizer 44 can also track a pose of the display device 100 in a common coordinate system with the physical object (O). The display device 100 can be tracked using a display tracker 102, or by any other suitable technique such as those described above. For instance, the display device 100 can be tracked using machine vision (e.g., with or without trackers), tracked using optical or non-optical techniques. Alternatively, or additionally, when equipped with a motorized adjustment system, the pose of the display device 100 can be determined based on kinematic data, and independent of the localizer 44, as will be described below.

The control system 60 controls the display device 100 to render the registered computer images (R) according to at least the tracked pose of the physical object (O) and the display device 100. Hence, the rendering of the computer images (R) is dependent upon at least the pose the physical object (O) and the pose of the display device 100. Specifically, referring to FIG. 2, a perspective of the rendering is based on a point or field of view (FOV) of a virtual camera (VC) that faces the plane (P) of display device 100. The field of view (FOV) can be based on a pinhole camera model projected towards the display device 100. The field of view (FOV) is also known as the viewing frustum (F), which will be described below.

A virtual position (VP) of the virtual camera (VC) is located on a side (S1) of the physical object (O) that is opposite from the side (S2) of the display device 100. Since the virtual camera (VC) is located in front of the plane (P) of the display device 100 in FIG. 2, the computer image (R) is showing the side of the physical object (O) at side (S1), rather than a mirrored view at side (S2).

The virtual position (VP) may be located at a predetermined distance (d) from the plane (P) of display device 100. The distance (d) is based on a Z-axis line drawn between the virtual position (VP) of the virtual camera (VC) and the plane (P). The Z-axis may be defined with reference to the virtual position (VP) or the display device 100. The virtual position (VP) can be anywhere on the virtual camera (VC) and can be defined by a single point or points, or any type of surface or volumetric geometry. In some examples, the virtual position (VP) remains fixed at a predetermined distance (d). Alternatively, the predetermined distance (d) can change in response to certain conditions. For example, the user can specify to the control system 60 a preference for the distance (d). The distance (d) can change automatically depending upon conditions such as, but not limited to: a type of surgical procedure, a certain step of the procedure, a tracked pose of the user's viewpoint (V), a tracked pose of the object, a tracked pose of the display device 100, a tracked pose of a tool 110, 20, or the like. In one example, the distance (d) can be defined at any suitable distance and within any suitable range, including, but not limited to between 1 meter and 5 meters, or any distance inclusively therebetween.

In one example, the virtual position (VP) of the virtual camera (VC) is transverse to the plane (P) of the display device 100. In other words, a Z-axis line drawn between the virtual position (VP) and the plane (P) of the display device 100 defines an angle relative to the plane (P) wherein the angle is in a range between 0 and 180 degrees. In a more specific implementation, the virtual position (VP) of the virtual camera (VC) is orthogonal to the plane (P) of the display device 100. In other words, a line drawn between the virtual position (VP) and the plane (P) of the display device 100 is 90 degrees normal to the plane (P). In other words, in this example, computer images (R) are rendered with an on-axis perspective projection orthogonal to the display device 100 from the given distance (d).

The virtual position (VP) of the virtual camera (VC) also has X and Y coordinate locations relative to the plane (P) of the display device 100. The X and Y coordinates may be defined with reference to the virtual position (VP) or the display device 100. In one example, the X and Y coordinates are defined in a plane that is parallel to the plane (P) of the display device 100. However, the X and Y coordinate plane need not be parallel to the plane (P), for example, if the virtual camera (VC) is projecting towards the display device 100 at a non-orthogonal angle.

Furthermore, whether projecting transverse or orthogonal to the display device 100, the line drawn between the virtual position (VP) and the plane (P) may be directed towards the geometrical center of the display device 100. Alternatively, the line drawn between the virtual position (VP) and the plane (P) may be offset from geometrical center of the display device 100. For example, the offset location can be towards a corner or edge of the display device 100. The X-Y placement of virtual position (VP) relative to the display device 100 can change in response to certain conditions. For example, the user can specify to the control system 60 a preference for X-Y placement of virtual position (VP). The X-Y placement of virtual position (VP) can change automatically depending upon conditions such as, but not limited to: a type of surgical procedure, a certain step of the procedure, a tracked pose of the user's viewpoint (V), a tracked pose of the object, a tracked pose of the display device 100, a tracked pose of a surgical tool 20, or the like. In one example, the distance (d) can be defined at any suitable distance and within any suitable range, including, but not limited to between 1 meter and 5 meters, or any distance inclusively therebetween.

Rendering of the computer images (R) based on the virtual camera (VC) is implemented using a viewing frustum (F) originating from the virtual camera (VC) and passing through an object, which in this case is the plane (P) of the display device 100. The viewing frustum (F) may be a region of space in a 3D modeled world that may appear on the display device 100 and may considered as the field of view of the virtual camera (VC). An apex of the frustum (F) is the zero-point originating from the virtual camera (VC) and may also be regarded as the virtual position (VP) of the virtual camera (VC). In one example, the plane (P) of the display device 100 may be located at a base (B) or far-clipping plane (FCP) of the viewing frustum (F). The viewing frustum (F) may comprise a near clipping plane (NCP) proximate to the virtual camera (VC). The far-clipping plane (FCP) and near-clipping planes (NCP) virtually cut the frustum (F) perpendicular to the viewing direction such that objects closer to the camera than the near-clipping planes (NCP) or beyond the far-clipping plane (FCP) are not rendered on the computer image (R). Objects that lie partially or completely outside of the viewing frustum (F) can be removed from the rendering process for processing efficiency. The computer images (R) on the display device 100 are projected based on the viewing frustum (F). The viewing frustum (F) can be based off any plane truncation or any suitable 3D-shape, including a pyramid, cone, or the like. The viewing frustum (F) can take any configuration other than that shown in the Figures or described herein.

In the FVF technique, the virtual position (VP) of the virtual camera (VC) is automatically updated by the control system 60 in response to (manual or motorized) adjustment to the pose of the display device 100. If the user moves or rotates the display device 100, the position of the virtual camera (VC) is automatically updated. Therefore, in contrast to the standard visualization displays within surgical navigation systems, the mental mapping of the real object to its image on the screen is simplified.

Figure 3A:
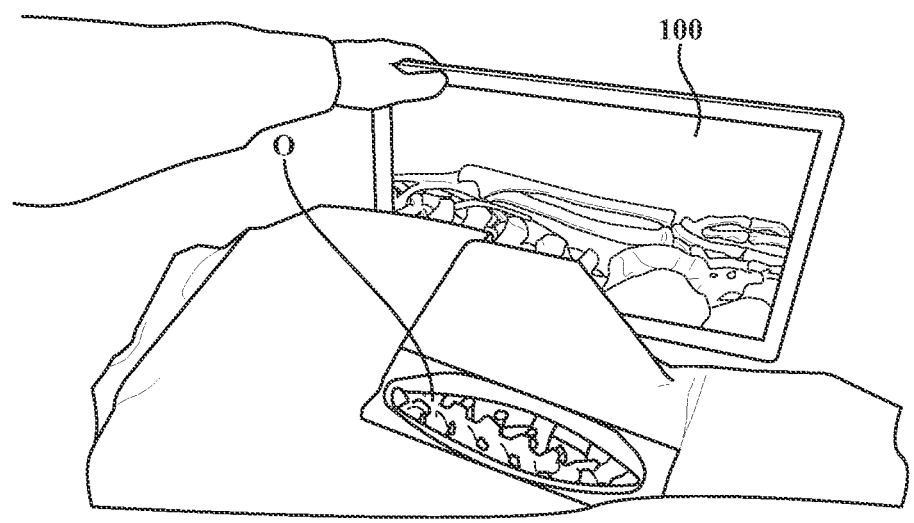
FIG. 3A is an illustrative real-world example taken from a first-person perspective of one implementation of the Fixed View Frustum visualization technique illustrating a user manually adjusting the display device to adjust the visualization of a 3D model of the physical object.
Figure 3B:
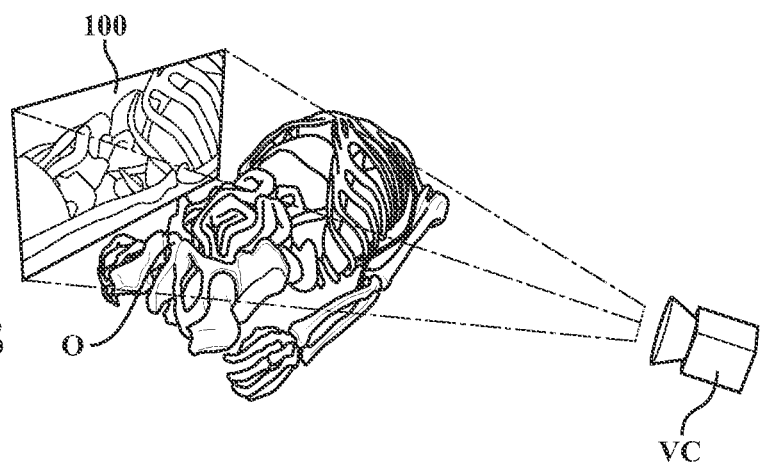
FIGS. 3B and 3C provide simulated illustrations of one implementation of the Fixed View Frustum visualization technique comparatively showing adjustment to the pose of the display device and virtual camera positions.
Figure 3C:
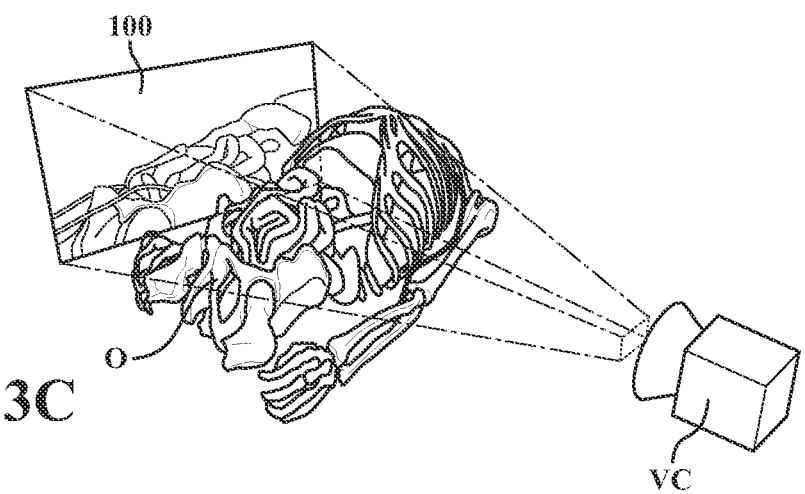

Examples of such Fixed View Frustum display visualizations are shown in FIGS. 3A-3C. An illustrative real-world example is shown in FIG. 3A and two simulations are shown in FIGS. 3B and 3C, respectively. FIG. 3A shows an operator moving the display device 100 by hand to visualize the internal virtual model (VM) of the physical object (O).

As the user adjusts the display device 100, the computer rendering (R) on the display device 100 updates accordingly. FIGS. 3B and 3C provide simulation illustrations of the FVF technique from two different viewpoints of the same configuration of the virtual camera (VC). As comparatively shown, the display device 100 changes pose between FIGS. 3B and 3C and the virtual position (VP) of the virtual camera (VC) updates accordingly. The computer image (R) also changes perspective in accordance with the relative positioning between the viewing frustum (F) and the physical object (O).

i. Screen Parallel Slice Visualization (SPSV)

Referring now to FIGS. 4-6, a Screen Parallel Slice Visualization (SPSV) sub-technique of the FVF method is described. While the FVF visualization is intuitive to use and can display 3D data, the technique can be further implemented using slice visualization. Accordingly, one can incorporate the slice view into the spatially-aware visualization concept described.

Figure 4A:
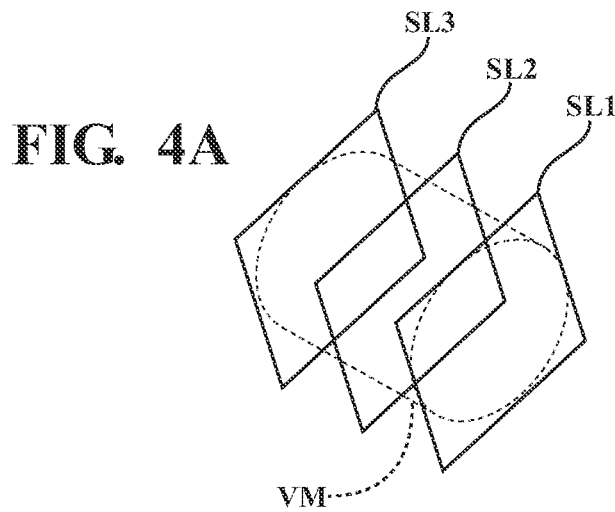
FIGS. 4A and 4B are diagrams illustrating implementation of the Screen Parallel Slice Visualization technique wherein slices of the 3D model of the object are obtained and displayed on the display device in parallel with the plane of the display device.

With reference to FIG. 4A, this can be achieved in one implementation by slicing a 3D virtual model (VM) of the physical object (O) into a plurality of slices (SL1, SL2, SL3 .... SLN). In one implementation, the slices (SL) are made at planes parallel to the plane (P) of the display device 100. The virtual model (VM) can be a CT model, X-ray model, MRI model or a model created using any other type of imaging technique. Alternatively, instead of slicing a 3D virtual model (VM), the imaging data of the physical object (O) may comprise a plurality of slices that can be obtained from computer-memory with or without having combined the same into a 3D model.

Figure 4B:
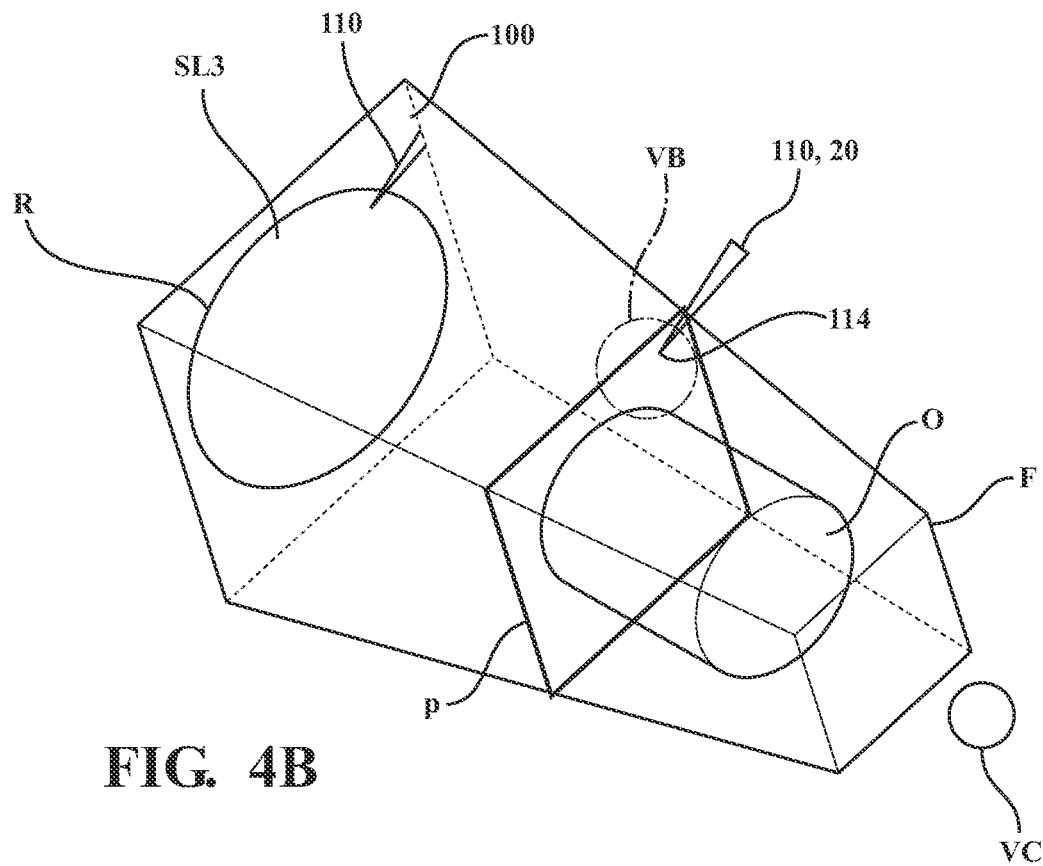
Figure 5A:
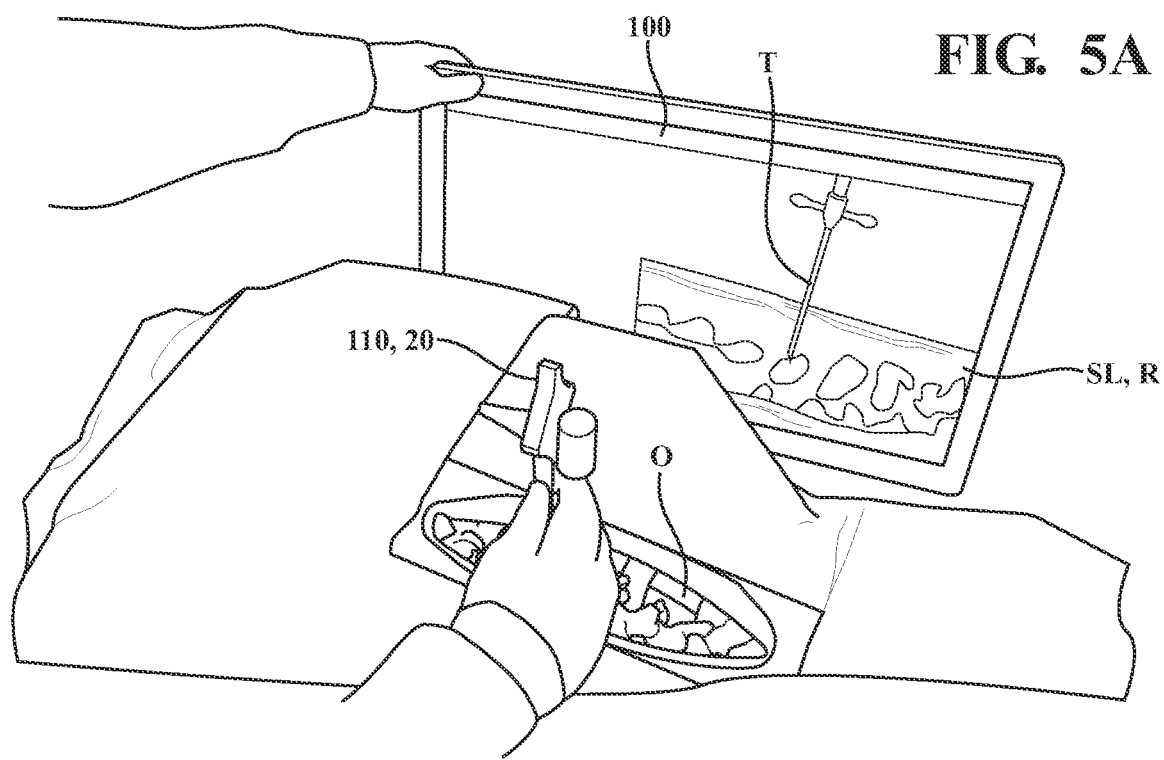
FIGS. 5A and 5B are illustrative real-world examples, taken from a first person perspective, of one implementation of the Screen Parallel Slice Visualization technique utilized in conjunction with the Fixed View Frustum visualization technique comparatively showing the user changing the pose of the display device which causes the slice to change perspective correspondingly.
Figure 5B:
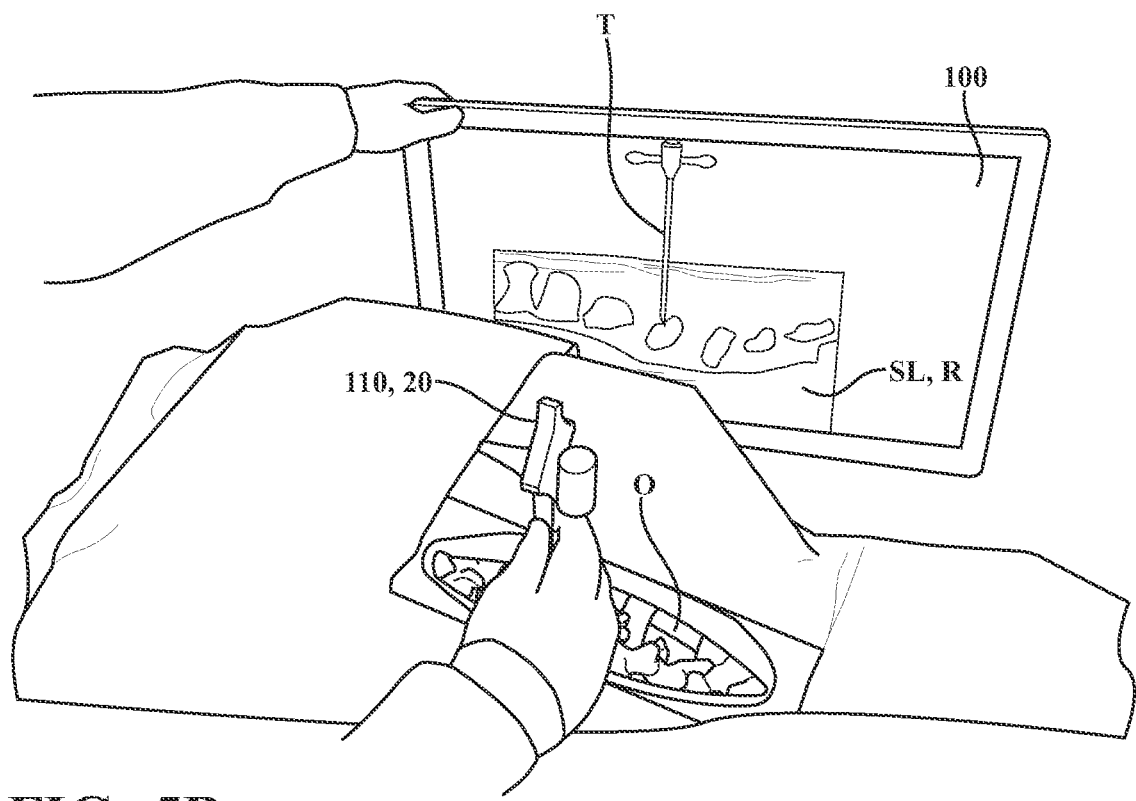

In one implementation, and with reference to FIG. 4B, the displayed slice (SL) can be based on a designated plane (p) sliced through the viewing frustum (F). The designated plane (p) can be fixed relative to the virtual camera (VC) position, or the designated plane (p) can dynamically change based on any of the conditions described herein. When the field of view of the virtual camera (VC) passes through the physical object (O), the control system 60 can immediately obtain the slice (SL) that corresponds to the intersection of the designated plane (p) with the physical object (O).

The orientation of the computer image (R) of the slice (SL) can be adjusted based on the pose of the display device 100. As shown comparatively between FIGS. 5A and 5B, the user is given the interaction method to rotate the display device 100, which in turn also rotates the slice (SL) and a virtual model (T) of the tool 110, 20. The physical object (O) and tool 110, 20 are in the same relative position in FIGS. 5A and 5B.

Alternatively, or additionally, as shown in FIG. 6, the orientation of the slice (SL) can be set based on a tool 110, 20 brought within the viewing frustum (F) of the virtual camera (VC). A pose of the tool 110, 20 can be tracked by the localizer 44 using any suitable means, such as those described herein. The computer images (R) that are rendered can include images of the tool 110, 20 and slice (SL) using the Fixed View Frustum method as discussed above. Alternatively, or additionally, the orientation of the slice (SL) can be set based on a user's perspective as defined by a tracked pose of a viewpoint tracking system (VTS), such as an external camera (C) facing the user or a head-mounted device 120 (described in detail below).

The displayed slice (SL) can be dynamically changed to different slices (SL) during use of these techniques. The slice (SL) can change depending on the pose of the physical object (O), the display device 100, or any combination thereof. Additionally, or alternatively, the slice (SL) can change using any of the input devices described herein. Also, as shown in FIG. 6, the tool 110, 20 can be utilized to change the slice (SL). For example, the tool's 110, 20 pose, position, and/or distance or orientation relative to either the physical object (O) or the display device 100, can automatically cause the control system 60 to change the slice (SL). In some implementations, portions of the slice (SL) can be displayed based on a (2D or 3D) virtual boundary (VB) that is associated with a tip 114 of the tool 110, 20, as shown in FIG. 4B. For instance, the virtual boundary (VB) can be defined by any shape (e.g., rectangle, box, circle or sphere) having any suitable dimension (e.g., a 200 mm diameter) with the tool tip 114 at the center of the boundary (VB). If the tool 110, 20 is moved towards the object (O) such that the object (O) intersects the virtual boundary (VB), the control system 60 can dynamically present or change the displayed slice (SL) that corresponds to the intersection. The slice (SL) can be presented in whole (as shown in FIG. 4B) or can be cropped (FIG. 6) depending upon the location of the virtual boundary (VB).

ii. Contextually Accurate Rendering

With reference to FIG. 7, the control system 60 is configured to render the computer images (R) in a contextually accurate manner. In other words, the computer image (R) rendering takes into account spatial layering of the object (O), tool 110, 20, and/or slice (SL) relative to one other in in the common coordinate system so as to mimic the actual spatial location of the same in the real coordinate system in which these items exist. As shown in FIG. 7, the tool 110, 20 is physically inserted into the object (O) and the display device 100 presents the virtual model (T) of the tool 110, 20 and the corresponding slice (SL) relative to a 3D model (VM) of the object (O). However, as shown, these renderings (R) layered based on the perspective of the virtual camera (VC). In other words, the virtual model (T) of the tool 110, 20 deliberately obstructed by corresponding portions of the 3D model (VM) of the object (O). In this case, the rib cage of the anatomy is obstructing the tool 110, 20 shaft. Similarly, the slice (SL) is displayed such that portions of the slice (SL) are obstructed by corresponding portions of the 3D model (VM) of the object (O). In this case, the slice (SL) is partially obstructed by several ribs. Although this technique obstructs portions of the visualization, it benefits the user to visualize the environment in a context that closely resembles real-world spatial positioning of the object (O), slice (SL) and tool 110, 20. This visualization technique can be utilized for any of the techniques described herein, including the FVF and SPSV techniques, as well as for any of the specific implementations, conditions, and/or situations described herein.

iii. Adjustment System

Figure 8:
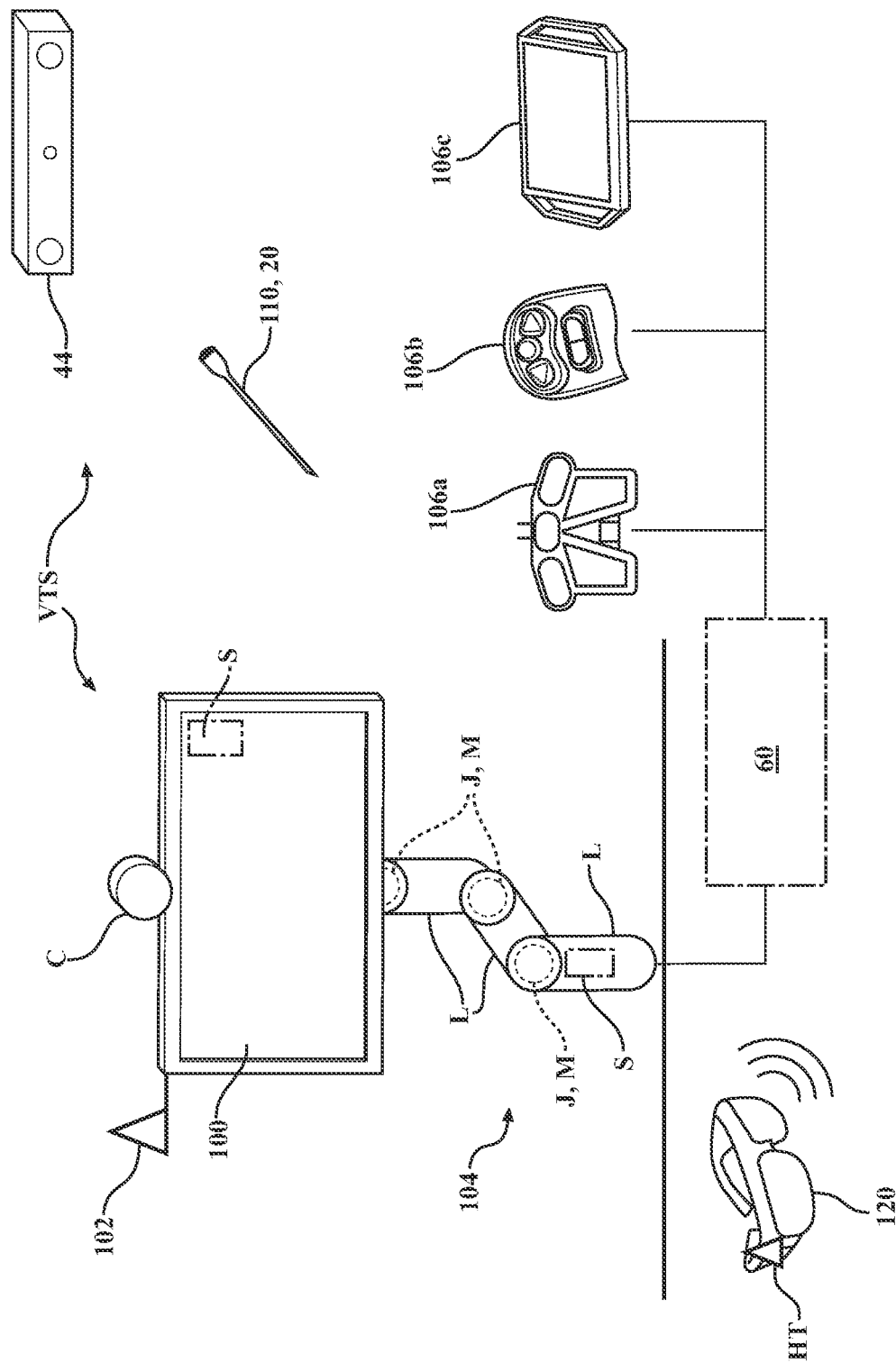
FIG. 8 is one implementation of an adjustment system that is configured to adjust the pose of the display device, for example, for use with the Fixed View Frustum visualization technique.

As shown in FIG. 8, the display device 100 may optionally be connected to an adjustment system 104. The adjustment system 104 can be passive or active and can comprise any features or possible configurations of the robotic manipulator 14 described above. For example, the adjustment system 104 may comprise a plurality of links (L), joints (J), and actuators (M) for driving the joints (J). The adjustment system 104 can be manually or automatically controlled to adjust a pose of the display device 100. The pose of the display device 100 can be moved in up to six-degrees of freedom (three translational and three rotational). Sensors(S) may be provided on any of the components of the adjustment system 104 to detect movement of the adjustment system 104. The control system 60 can utilize measurements from the sensors(S) to kinematically derive the pose of the display device 100. This can be done in addition to or alternatively from using the localizer 44. The sensors(S) can be any suitable configuration, including, but not limited to: motor current sensors, joint position sensors or encoders (rotary, absolute, incremental, virtual-absolute, etc.), optical sensors, inertial sensors (accelerometer, inclinometer, gyroscope, etc.) or the like. Any of the sensors(S) can also be provided on the display device 100 itself.

In some instances, as shown in FIG. 8, one or more user input devices 106 can be wired or wirelessly connected to the control system 60 to enable the user to control the pose of the display device 100. The input devices 106 include but are not limited to: a foot pedal 106*a*, a hand-held pendant 106*b*, display input 106*c* such as a tablet, smartphone, or display of the navigation system, the tool 110, 20, and/or a viewpoint tracking system (VTS), such as an external camera (C) facing the user or a head-mounted device 120. The input devices can also be any of those described above, including but not limited to: push buttons, sensors, switches, keyboard, mouse, microphone (voice-activation), gesture control devices, touchscreens, joysticks, etc. The input device 106 receives a command from the user and the control system 60 directs the one or more actuators M to adjust the joints J and ultimately the pose of the display device 100 in accordance with the command.

The tracked tool 110, 20 can also be utilized for triggering the control system 60 to control the adjustment system 104. In one implementation, the pose of the tracked tool 110, 20, whether it be position and/or orientation, or any derivate thereof (velocity, acceleration, etc.) can cause the control system 60 to adjust the pose of the display device 100. For example, the tracked pose of the tool 110, 20 can be compared to the virtual position (VP) of the virtual camera (VC), the viewing frustum (F), the plane (P) of the display device 100, or any combination thereof. The control system 60 can assess this comparison relative to a threshold condition or measurement. If the control system 60 determines that the tool 110, 20 has moved in a manner that meets or exceeds the threshold condition, the control system 60 can command the adjustment system 104 to adjust the display device 100. This may be beneficial for various situations, including, but not limited to: the tool 110, 20 moving towards or away from the object (O), the tool 110, 20 moving in/out of the viewing frustum (F), keeping the tool 110, 20 within view of the virtual camera (VC), or the like.

With continued reference to FIG. 8, the head-mounted device 120 can also be utilized for triggering the control system 60 to control the adjustment system 104. In one implementation, the pose of the head-mounted device 120 is tracked using any tracking technique described herein, or equivalents thereof. The tracked pose of the head-mounted device 120, whether it be position and/or orientation, or any derivate thereof (velocity, acceleration, etc.) can cause the control system 60 to adjust the pose of the display device 100. For example, the tracked pose of the head-mounted device 120 can be compared to the virtual position (VP) of the virtual camera (VC), the viewing frustum (F), the plane (P) of the display device 100, or any combination thereof. The control system 60 can assess this comparison relative to a threshold condition or measurement. If the control system 60 determines that the head-mounted device 120 has moved in a manner that meets or exceeds the threshold condition, the control system 60 can command the adjustment system 104 to adjust the display device 100. This may be beneficial for various situations, including, but not limited to: the head-mounted device 120 moving towards or away from the object (O), the head-mounted device 120 moving in/out of the viewing frustum (F), keeping the head-mounted device 120 within view of the virtual camera (VC), or the like.

Additionally, or alternatively, any other viewpoint tracking system (VTS), such as an external camera (C) facing the user can be utilized to track the user's viewpoint (V) for triggering the control system 60 to control the adjustment system 104.

The adjustment system 104 can be utilized for any of the techniques described herein, including the FVF and SPSV techniques, as well as for any of the specific implementations, conditions, and/or situations described herein.

B. Dynamic Mirror View Frustum Visualization Technique

With reference to FIGS. 9-12, another example visualization method that can be utilized with the surgical system 10 comprises a Dynamic Mirror View Frustum (DMVF) for aiding in user interaction with the physical object (O).

As will be understood from the description below, there are technical similarities between the FVF and DMVF techniques. Accordingly, any and all of the above description related to the system 10, the FVF technique, and any physical, computational, and/or any techniques associated therewith are fully incorporated by reference for use with and can be applied by the DMVF technique described herein and hence are not repeated for simplicity of description.

Figure 9:
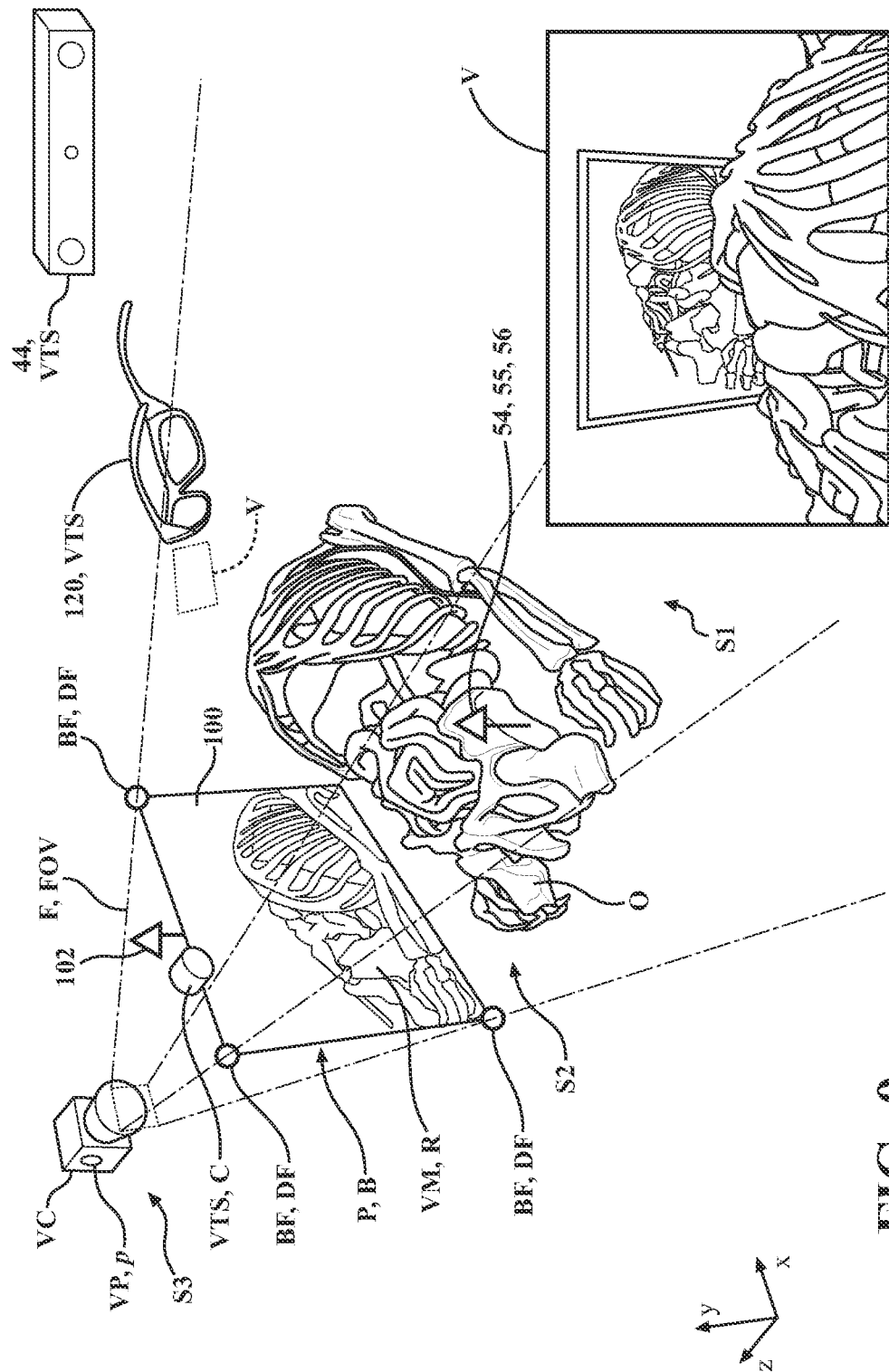
FIG. 9 is a simulated illustration of one implementation and setup of a Dynamic Mirror View Frustum visualization technique wherein the perspective of the images displayed depend on the pose of the display device, the pose of the object and the pose of a user's viewpoint to enable the displayed images to be rotated and sized to match the user's point of view.

For the DMVF technique, and with reference to FIG. 9, the display device 100 defines the plane (P). The physical object (O) is located in front of the plane (P). In other words, the physical object (O) is located in front of the displayed screen of the display device 100.

The user viewing the display device 100 is also located in front of the plane (P). The user's viewpoint (V) is tracked utilizing a viewpoint tracking system (VTS). In one implementation, the viewpoint tracking system (VTS) includes a camera (C) facing the user. The viewpoint tracking system (VTS) can the navigation system itself or can be part of or separate from the navigation system. The camera (C) can be the localizer 44 or a separate device. The camera (C) can be mounted to the display device 100, or elsewhere. The control system 60 can receive signals from the camera (C) and recognize changes to position and/or orientation of the user's face, eyes, head, or other feature using pose estimation algorithms.

In another implementation, the viewpoint tracking system (VTS) additionally or alternatively includes a head-mounted device 120 that is provided directly on the user. The head-mounted device 120 is located in front of the plane (P) and in front of the displayed screen of the display device 100. In one configuration, the head-mounted device 120 is located on a first side (S1) of the physical object (O) and the display device 100 is located on a second opposing side (S2) of the physical object.

The head-mounted device 120 comprises one or more trackable features (HT) such that its pose can be tracked by the navigation system 32 and/or control system 60. The trackable features (HT) can be any type described above or any equivalents thereof. In this technique, the head-mounted device 120 is any device that is configured to enable tracking the pose of the user's point of view. Here, pose means position of the head-mounted device 120, and optionally, position and orientation. The user's point of view can be defined by the general field of view of the user's vision, the direction in which the user turns his/her head, and/or the gaze of the user's eyes. The head-mounted device 120 can be or include one or more trackers attached to any part of a user's head and/or eye or head wear such as glasses (such as those shown in FIG. 8 for example), goggles, head-band helmet, contact lenses, or the like. In one example, the head-mounted device 120 is an optical-see-through head-mounted-display. Other examples of the head-mounted device 120 are contemplated. In FIG. 9, the viewpoint (V) derived from tracking the head-mounted device 120 is shown as a rectangle for simplicity and the viewpoint is facing the display device 100.

Just as with the FVF technique, the navigation system 32 and/or control system 60 registers computer images (R) to the physical object (O). The navigation system 32 and/or control system 60 track a pose of the physical object (O), the display device 100, and the user's viewpoint (V) relative to one another in a common coordinate system. The display device 100 is controlled for rendering the registered computer images (R) according to the tracked pose of the physical object (O), the display device 100, and the user's viewpoint (V). In other words, the pose of each of these items can affect how the computer images (R) are displayed.

A perspective of the computer image (R) is based on a field of view or viewing frustum (F) of a virtual camera (VC) that has a virtual position (VP) behind the plane (P), shown as side (S3) in FIG. 9, which is behind the display device 100. The virtual camera (VC) faces the rear of the display device 100 and faces the viewpoint of the user as derived from the viewpoint tracking system (VTS). The physical object (O), the display device 100, and the user's viewpoint (V) are at least partially within the viewing frustum (F) in FIG. 9. Since the virtual camera (VC) is located behind the plane (P) of the display device 100, the rendering (R) provides visualization as though the display device 100 were a mirror relative to the viewpoint of the user. In FIG. 9, the computer image (R) is showing the side of the physical object (O) at side (S2).

The virtual position (VP) of the virtual camera (VC) is automatically updated in response to adjustment to the tracked pose of the user's viewpoint (V). The user can move left and right or back and forth and see the physical object (O) and any tool 110, 20 moving correspondingly on the mirror-like rendering (R) of the display device 100. By knowing the poses of the physical object (O), the display device 100, and the user's viewpoint (V), the control system 60 is able to create the computer images (R) such that they obey the same laws as a real mirror.

Figure 10A:
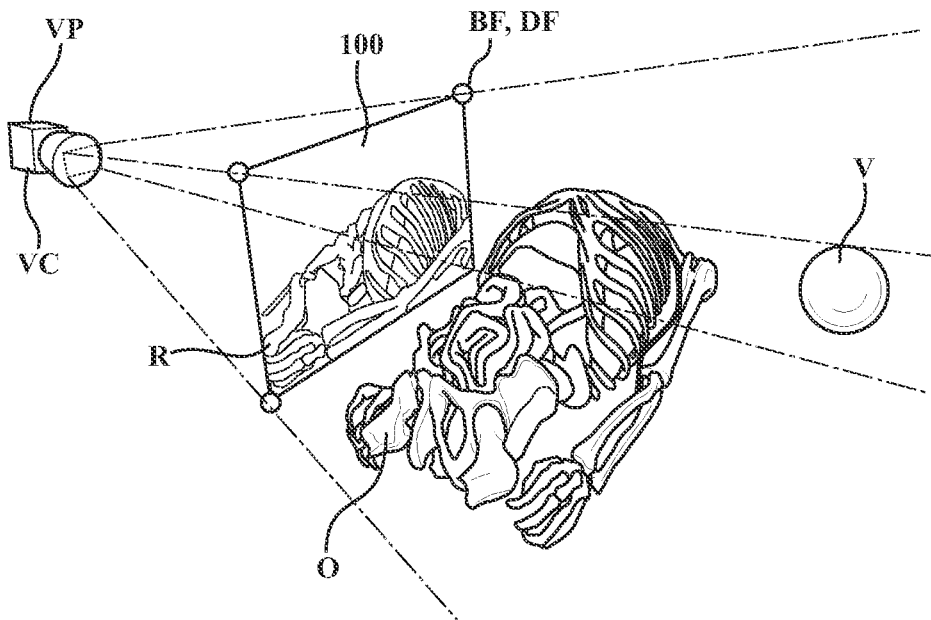
FIGS. 10A and 10C provide simulated illustrations of one implementation of the Dynamic Mirror View Frustum visualization technique comparatively showing from a 3rd person view changes to the pose of the respective user viewpoint and virtual camera positions.
Figure 10B:
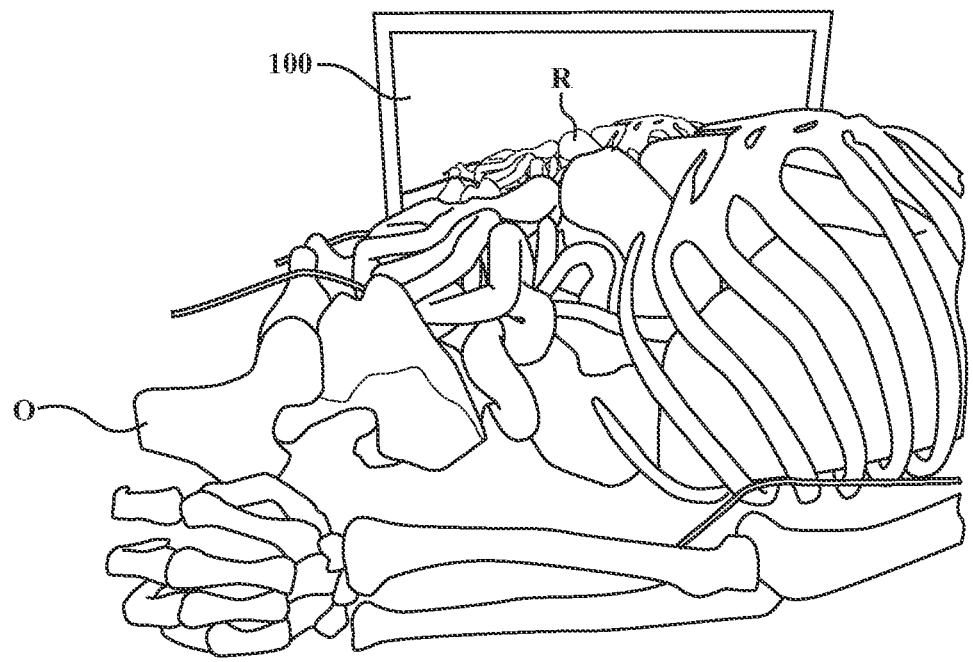
FIGS. 10B and 10D illustrate the environment of FIGS. 10A and 10C, respectively, as taken from a 1st person perspective.
Figure 10C:
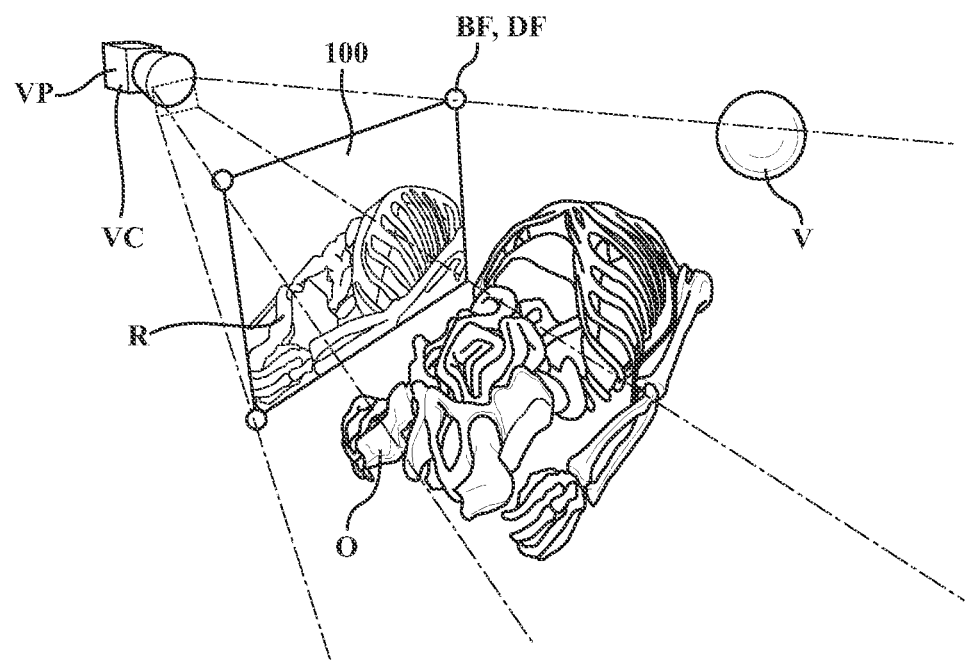
Figure 10D:
Figure 10E:
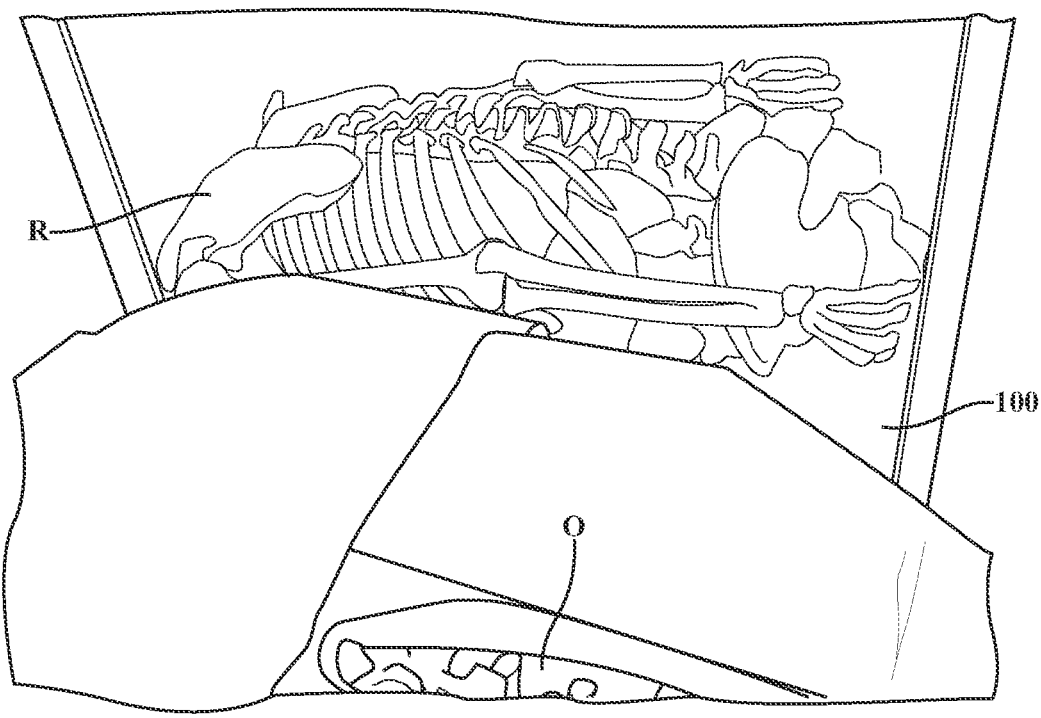
FIGS. 10E and 10F are illustrative real-world examples of one implementation of the Dynamic Mirror View Frustum visualization technique, taken from 1st person perspective, and comparatively showing changes to the user's perspective relative to the display device causing the displayed images to be rotated and sized to match the user's point of view.
Figure 10F:
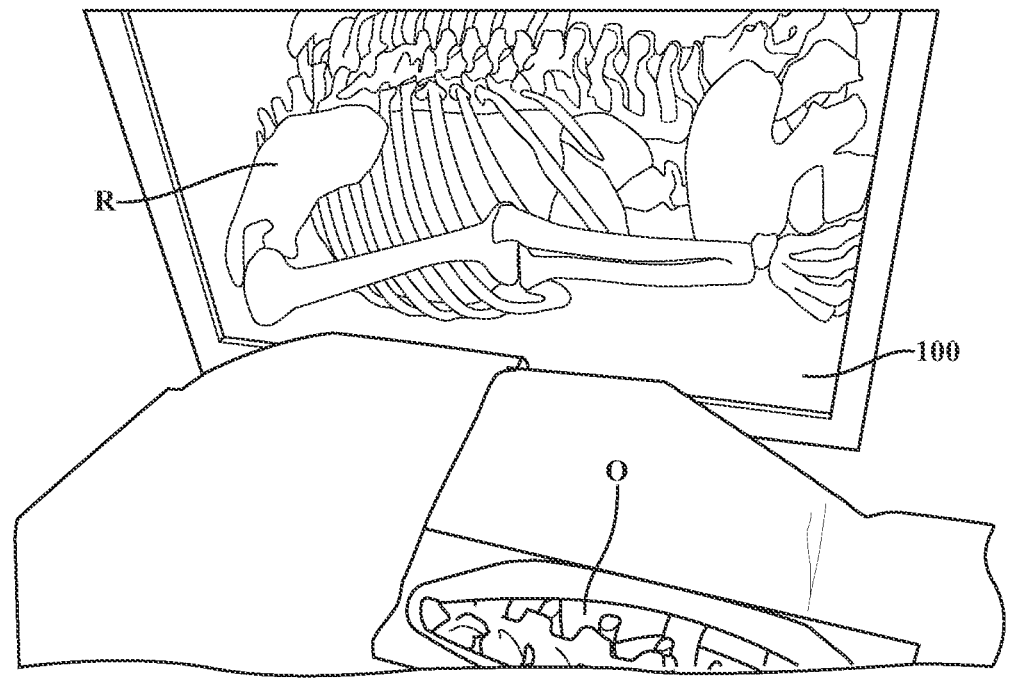

FIG. 10A-10F illustrate examples of the DMVF technique. Specifically, simulated mirror views are shown in FIGS. 10A-10D and real-world illustrative examples are shown in FIGS. 10E and 10F. Comparing the third person views, as shown in FIGS. 10A and 10C, the virtual position (VP) of the virtual camera (VC) changes depending on user's viewpoint (V) (shown as a sphere) as derived from viewpoint tracking system (VTS). FIG. 10B shows the first-person viewpoint of what would be seen on the display device 100 in the scenario of FIG. 10A. FIG. 10D shows the first-person viewpoint of what would be seen on the display device 100 in the scenario of FIG. 10C.

The display device 100 shows the objects in front of the display just like a mirror would do, taking the poses of the screen, objects, and the user viewpoint into account. This paradigm works can contribute to a more intuitive visualization of the physical object (O) by using motion parallax and observing structures from additional desired viewpoints. The user gains the freedom to interact with the data just by looking, without necessarily requiring an interaction device like a mouse or joystick. As the users do not constantly need to redefine their view on the object (O), the user is enabled to toggle the interactivity on or off for example with any input device, such as a foot pedal. The user can change the visualization in a hands-free manner. Since the natural human visual system is adapted to looking at real mirrors, the DMVF visualization provides an intuitive interface. DMVF also facilitates exploring and defining the best slice (SL) or rendering (R) for a given navigation task. The slice (SL) or rendering (R) can remain fixed during the surgical action until further data exploration is desired.

i. Virtual Camera and Mirror Frustum Setup for DMVF

The virtual position (VP) of the virtual camera (VC) dynamically changes in the DMVF method depending upon at least the tracked pose of the user's viewpoint (V). In one implementation, the viewpoint of the virtual camera (VC) can be derived as described herein. In one example, the control system 60 moves the virtual camera (VC) according to a projection matrix that is adjusted so that the viewing frustum (F) is fitted such that boundary features (BF) of the frustum (F) coincide with the features (DF) of the display device 100. The features (DF) of the display device 100 comprise points or other geometry which encode a size, aspect ratio, position and orientation of the display device 100 in the common or world coordinate system. In the example of FIG. 9, wherein the viewing frustum (F) comprises a truncated four-sided pyramid and the display device 100 is rectangular, the boundary features (BF) of the viewing frustum (F) are points on the edges of the sides of the pyramid and the features (DF) are the fixed corners of the display device 100. Hence, the points on the edges of the viewing frustum (F) are made to coincide with the corners of the display device 100 for any positional movement of the virtual camera (VC) in the coordinate system. Of course, this configuration may change depending on the geometry of the viewing frustum (F) and the display device 100. This results in a warped image (R), which appears in correct perspective as a mirror reflection from the tracked pose of the user's viewpoint (V).

From the virtual position (VP) of the virtual camera (VC), a mirrored world position of the viewpoint $p_{mirrored}$ can be calculated as follows: define the normal to the mirror plane (P) as (0; 0; 1). In its local coordinate system, the mirroring corresponds to multiplication with the matrix $M_{flip}$ which is expressed in [1] and which considers the fixed features (DF) of the display device 100 (i.e., in this case the four corners).

$$M_{flip} = \begin{vmatrix} 1 & 0 & 0 & 0 \\ 0 & 1 & 0 & 0 \\ 0 & 0 & -1 & 0 \\ 0 & 0 & 0 & 1 \end{vmatrix} \quad [1]$$

This is equivalent to scaling by −1 in z-direction. Let us assume, according to one implementation, that to provide the mirror view, the rendering depends on the position, and not the orientation, of the user's viewpoint (V) with respect to the mirror plane (P). A first transform is performed to transform a world position of the virtual camera (VC) viewpoint p into local coordinates of the mirror. This causes rotation of the frustum (F) to the viewpoint of the user. Then mirroring is performed with matrix $M_{flip}$ which provides perspective projection relative to the display device 100. Lastly, the mirrored local coordinates of the mirror are transformed back to the world position of the virtual camera (VC) viewpoint p which translates the user's viewpoint (V) to the apex of the viewing frustum (F). The result is a projection matrix expressed by:

$$p_{mirrored} = \text{Mirror}_{T_{World}} \cdot M_{flip} \cdot \text{World}_{T_{Mirror} \cdot p} \quad [2]$$

In the equation expressed in [2], the notation $A_{T_B}$ is utilized to represent a transformation from coordinate system A into B. This computation enables re-alignment or rotation of the base (B) or far-clipping plane (FCP) of the frustum (F) from an otherwise XY coordinate aligned position relative to the display device 100 to an alignment that is positioned relative to the user's viewpoint (V). Thereafter, the user viewpoint-aligned base (B) or far-clipping plane (FCP) is re-aligned back to the XY coordinates of the display device 100 such that an off-axis projection matrix can be applied to apply perspective rendering of the computer images (R).

To enable the computer images (R) on the display device 100 to render mirror views of the physical object (O) or tools 110, 20 in front of the display device 100 in relation to the user's pose, the off-axis projection matrix can be employed in one implementation. Here off-axis means that a line drawn from the user's viewpoint (V) to the display device 100 would not be at the geometrical center of the display device 100, but rather off-center. In such situations, the viewing frustum (F) becomes asymmetric and will change shape as the user's viewpoint (V) changes. The location at which the user's viewpoint (V) relative to the geometry of the plane (P) of the display device 100 can be monitored by the control system 60. As the frustum (F) shape changes depending upon the user's viewpoint (V), the boundary features (BF) of the viewing frustum (F) change. In one implementation, the viewing frustum (F) can be recomputed and/or updated at frequent intervals, such as, e.g., at every frame, as the pose of the display device 100 and/or the viewpoint of the user are likely to change.

The off-axis projection matrix has the mirrored viewpoint p at the apex of the viewing frustum (F) and the base (B) matching the surface or plane (P) of the display device 100. The viewing frustum (F) is rotated to align with the user's viewpoint (V). This takes the position of the viewpoint into account and warps the image so that it appears like a projection onto a tilted plane relative to the plane (P) of the display device 100. The effect of the changed viewpoint of the user on the frustum (F) together with the warped images, can be seen in FIGS. 10A, 10B as compared with FIGS. 10C, 10D. This implementation relies on a graphic API to set the projection matrix with the frustum (F) defined by the near clipping plane (NCP) coordinates in view space, which is then rotated to be non-perpendicular and moved to be located at the mirrored viewpoint. In other words, the base (B) of the frustum (F) is dynamically modified rotate out of the X-Y plane of the plane (P) of the display device 100 and positioned corresponding to the angle of the user's viewpoint (V) as derived from the viewpoint tracking system (VTS).

The calculation provided above provides one implementation of virtual camera (VC) setup for DMVF. However, there may be alternative manners of dynamically changing the virtual position (VP) of the virtual camera (VC) depending upon at least the user's viewpoint (V), without departing from the scope of the concept. For example, it is possible to align the base (B) of the frustum (F) to the display device 100. Boundary features (BF) of the viewing frustum (F) may exceed the geometry of the display device 100. In such instances, the control system 60 may limit the boundary features (BF) of the viewing frustum (F) relative to the geometry of the display device 100.

Figure 11A:
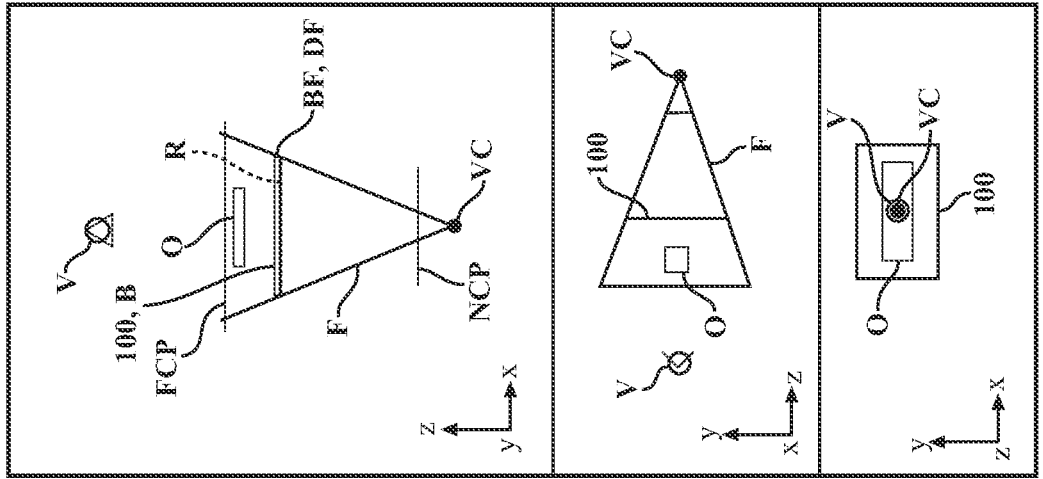
FIGS. 11A-11C are diagrams illustrating, in various views of the X,Y,Z coordinate system, one implementation of the Dynamic Mirror View Frustum visualization technique comparatively showing, for three scenarios, changes to the pose of the respective user viewpoint and virtual camera positions and rotation of the image rendering to align to the user's perspective.
Figure 11B:
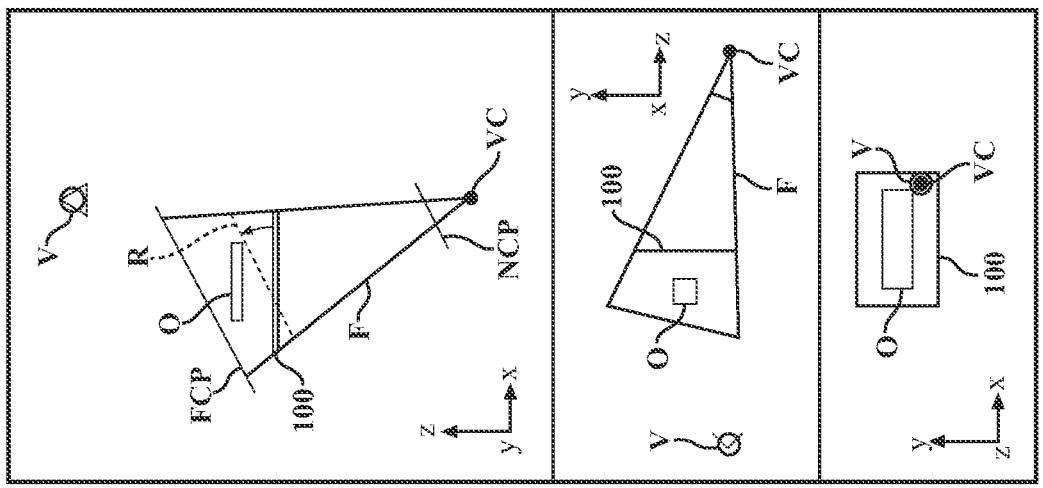
Figure 11C:
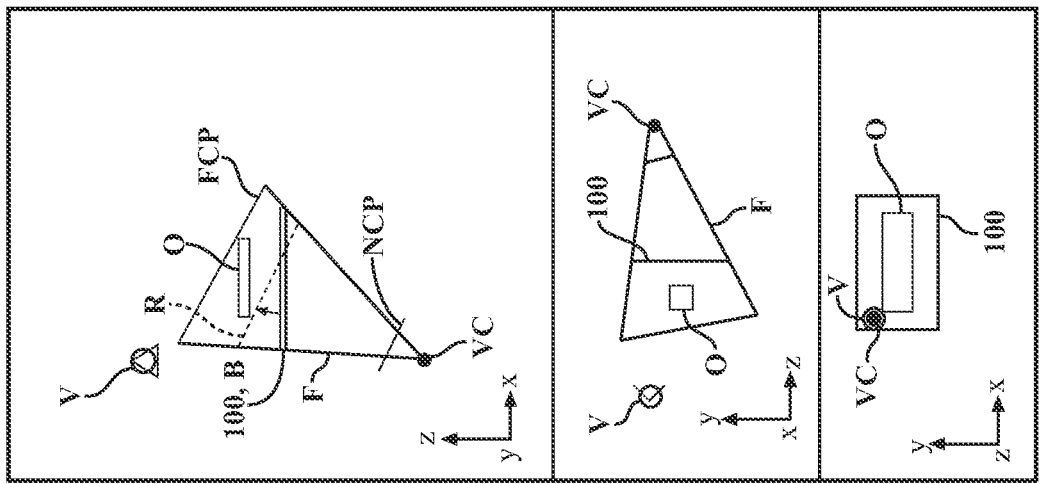

FIGS. 11A-11C compare, in various views of the X,Y,Z coordinate system, the relative positioning between the virtual camera (VC) and frustum (F), user's viewpoint (V), display device 100 and object (O) among three example scenarios. In these examples, the position of the virtual camera (VC) and the user's viewpoint (V) can be mirrored relative to the plane (P) of the display device 100 for each of the X, Y, and Z axes individually. For instance, the virtual camera (VC) and the user's viewpoint (V) are substantially equal distance apart from the display device 100 in each of the X, Y, and Z-directions. When visualized from the X-Y plane, the position of the virtual camera (VC) and the user's viewpoint (V) appear to coincide as result of this mirroring effect. However, perfect mirroring is not required in all implementations and the distance of (VC) and (V) to the display device 100 may not be equal for each of the axes and such distances can be customized or changed.

In FIG. 11A, the user's viewpoint (V) is on-axis at given position relative to the display device 100. The base (B) of the frustum (F) of virtual camera (VC) aligns with the X-Y plane of the display device 100. The projection renders computer images (R) that are centered and aligned to the user's centered viewpoint.

In FIG. 11B, the user's viewpoint (V) is moved to the left of center (from the user's perspective) and moved away from the display device 100 further than the given position of FIG. 11A. This relative change in motion of the user's viewpoint (V) causes the virtual camera (VC) to change correspondingly. In other words, the virtual camera (VC) moves to the right and away from the display device 100 (from the virtual camera's perspective). This correctly positions the virtual camera (VC) relative to the user's viewpoint (V). The viewing frustum (F) is rotated (counter-clockwise as seen from above) out of the X-Y plane of the display device 100 to the align to the user's viewpoint (V). In some instances, modification of the frustum (F) causes the far-clipping plane (FCP) to move further from the apex of the frustum (F) in response to the position of the virtual camera (VC) moving away from the display device 100. The projection renders computer images (R) that are rotated to align to the user's off-center viewpoint. The computer images (R) also render objects, such as the physical object (O) within the frustum (F) to be smaller in size as compared to FIG. 11A since the position of the user's viewpoint (V) is further away from the display device 100.

In FIG. 11C, the user's viewpoint (V) is moved to the right (from the user's perspective) and moved closer to the display device 100 than the given position of FIG. 11A. This relative change in motion of the user's viewpoint (V) causes the virtual camera (VC) to move to the left and closer to the display device 100 (from the virtual camera's perspective). This correctly positions the virtual camera (VC) relative to the user's viewpoint (V). The viewing frustum (F) is rotated (clockwise as seen from above) out of the X-Y plane of the display device 100 to the align to the user's viewpoint (V). In some instances, modification of the frustum (F) causes the far-clipping plane (FCP) to move closer to the apex of the frustum (F) in response to the position of the virtual camera (VC) moving closer to the display device 100. The projection renders computer images (R) that are rotated to align to the user's off-center viewpoint. The computer images (R) also render objects, such as the physical object (O) within the frustum (F) to be larger in size as compared to FIG. 11A since the position of the user's viewpoint is closer to the display device 100.

The dimensioning of the components of the FIG. 11 are merely provided for illustrative purposes and may not be exactly to scale. Furthermore, although the X-Z plane is shown illustrating lateral motion among the user's viewpoint and virtual camera (VC), the principles described herein may apply fully to vertical motion between the same in the X-Y plane.

ii. Viewpoint Facing Slice Visualization

Figure 12A:
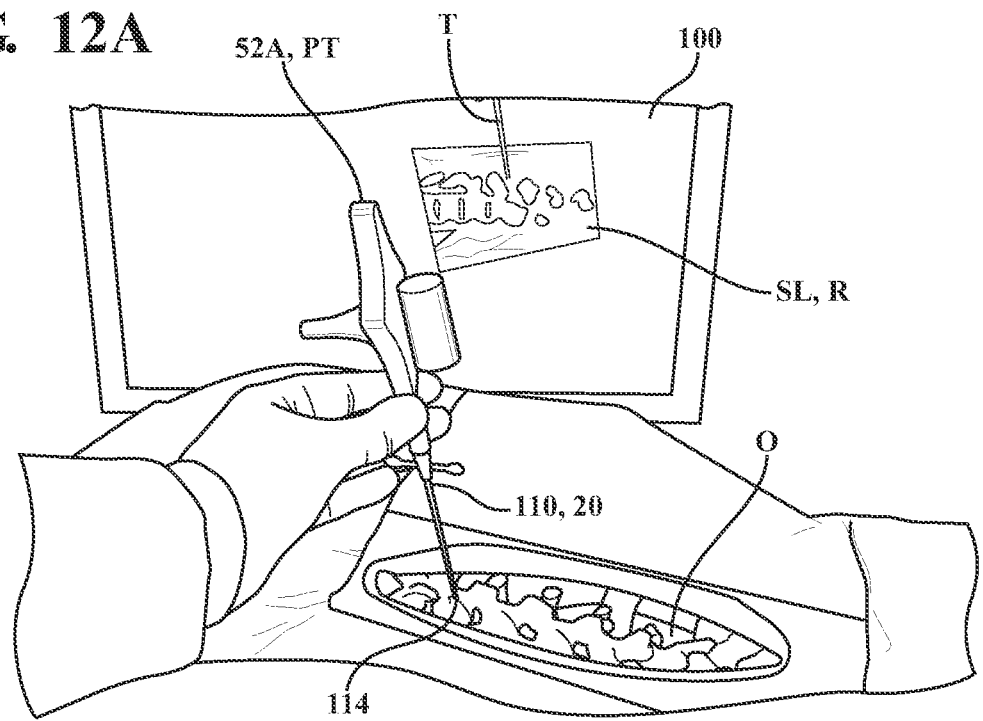
FIGS. 12A and 12B are illustrative real-world examples, taken from a 1st person perspective, of one implementation of a Viewpoint Facing Slice Visualization technique utilized in conjunction with the Dynamic Mirror View Frustum visualization technique comparatively showing the how changing the user's viewpoint relative to the display device causes the displayed slice to change perspective to align to the user's viewpoint.
Figure 12B:
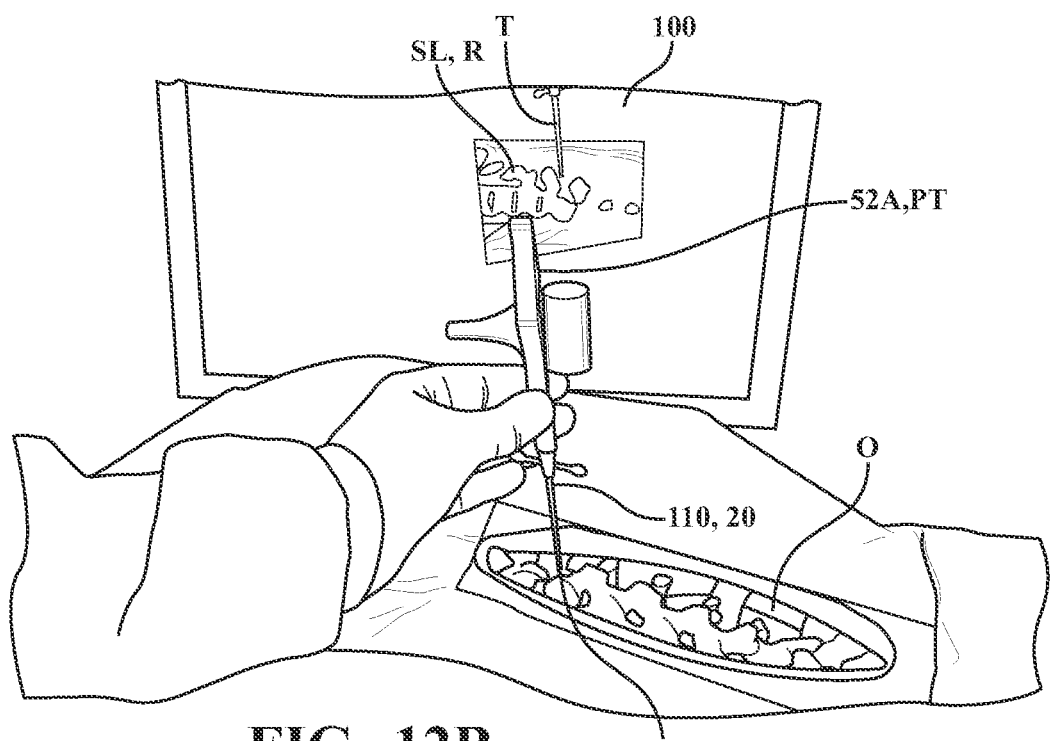

Referring now to FIGS. 12A and 12B, a Viewpoint Facing Slice Visualization (VFSV) sub-technique of the DMVF method is described. While the DMVF visualization is intuitive to use and can display 3D data, it is contemplated to further incorporate the slice view into the spatially-aware DMVF visualization concept described.

The slicing of the data can occur according to any of the techniques described above with respect to the SPSV technique and as shown with respect to FIGS. 4A and 4B, and hence, are not repeated herein for simplicity. Furthermore, the selection of the displayed slice (SL) can occur according to any of the techniques described above with respect to the SPSV technique and as shown with respect to FIGS. 4A and 4B.

In one implementation, the tool 110, 20 can be utilized to change the slice (SL). For example, the tool's 110, 20 pose, position, and/or distance or orientation relative to either the physical object (O) or the display device 100, can automatically cause the control system 60 to change the slice (SL). In some implementations, portions of the slice (SL) can be displayed based on a (2D or 3D) virtual boundary (VB) that is associated with a tip 114 of the tool 110, 20, as shown in FIG. 4B. For instance, the virtual boundary (VB) can be defined by any shape (e.g., rectangle, box, circle or sphere) having any suitable dimension (e.g., a 200 mm diameter) with the tool tip 114 at the center of the boundary (VB). If the tool 110, 20 is moved towards the object (O) such that the object (O) intersects the virtual boundary (VB), the control system 60 can dynamically present or change the displayed slice (SL) that corresponds to the intersection. The slice (SL) can be presented in whole (as shown in FIG. 4B) or can be cropped (FIG. 6) depending upon the location of the virtual boundary (VB).

Additionally, or alternatively, the slice (SL) may be changed depending on the pose of the physical object (O), the display device 100, user's viewpoint or any combination thereof. The slice (SL) may be changed using any of the input devices 106 described herein.

The orientation of the slice (SL) can be manipulated according to several different techniques. In the VFSV technique, the control system 60 tracks the display device 100 and the user's viewpoint (V) according to the DMVF technique. A position of the slice (SL) is based on the tracked position of the tool 110, 20. The orientation of the slice (SL), however, is chosen to point towards the mirror viewpoint. This guarantees that the slice (SL) faces the user when viewed through the mirror. That is, the slice (SL) is oriented to face the user's viewpoint (V) as derived by the viewpoint tracking system (VTS). The orientation of the slice (SL) rendered using the DMVF technique described above. That is, to accurately account for the user's viewpoint (V) relative to the display device 100, the slice (SL) is rotated relative to the plane (P) of the display device 100 and projected to be smaller or larger.

An example of the VFSV technique from two different first-person viewpoints can be seen in FIGS. 12A and 12B, wherein the tool 110, 20 remains stationary between FIGS. 12A and 12B. In FIG. 12B, the user's viewpoint (V) is moved slightly to the left, and closer to the tool 110, 20. The distance of the user's viewpoint (V) to the display device 100 remains about the same. In this example, the displayed slice (SL) appears to be the same to the user since the slice (SL) has rotated to correspond to the lateral motion of the user's viewpoint (V). If the user in FIG. 12B were to approach the display device 100, the slice (SL) will appear correspondingly larger, and vice-versa.

While the user's viewpoint (V) is utilized to implement the VFSV technique, the orientation of the computer image (R) of the slice (SL) can additionally be adjusted based on the pose of the display device 100, the pose of the object (O) and/or the pose of the tracked tool 110, 20 brought within the viewing frustum (F) of the virtual camera (VC).

Additionally, the control system 60 is configured to render the computer images (R) in a contextually accurate manner for the VFSV technique. In other words, the computer image (R) rendering takes into account spatial layering of the object (O), tool 110, 20, and/or slice (SL) relative to one other in in the common coordinate system so as to mimic the actual spatial location of the same in the real coordinate system in which these items exist. Hence, any of the description above related to the contextually accurate rendering for the SPSV technique, including the visualization of FIGS. 6 and 7 can be applied in its entirety to the VFSV technique and is not repeated for simplicity in description.

C. Visualization Mode Switching

The control system 60 can enable switching between any of the visualization modes described herein at any time and in response to any input or condition. For example, the control system 60 can enable switching between any of the following: FVF and DMVF visualizations; SPSV and the VFSV visualizations; 3D model visualization (without slices) using FVF visualization and using the SPSV technique (with or without the 3D model); 3D model visualization (without slices) using the DMVF technique and visualization using the VFSV technique (with or without the 3D model); static visualization and any of the FVF, SPSV, DMVF and VFSV techniques.

The switching between visualization modes can occur depending on user input. For example, the control system 60 can receive a command from any of the input devices 106 described herein, which include but are not limited to: a foot pedal 106a, a hand-held pendant 106b, display input 106c such as a tablet, smartphone, display device 100 or display of the navigation system, the tool 110, 20, and/or a head-mounted device 120, push buttons, sensors, switches, keyboard, mouse, microphone (voice-activation), gesture control devices, touchscreens, joysticks, etc.

The switching between visualization modes can occur automatically depending upon conditions such as, but not limited to: a type of surgical procedure, a certain step of the procedure, a tracked pose of the user's viewpoint (V) or head-mounted device 120, a tracked pose of the object (O), a tracked pose of the display device 100, a tracked pose of a tool 110, 20, or any combination thereof.

Several implementations have been discussed in the foregoing description. However, the implementations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

D. Case Study and Experimental Results

As proof of the concept, a confidential case study was performed with three trauma surgeons (chief surgeon, attending physician, and resident). The set up included a 3D-printed patient phantom, a display device 100 on an adjustable desk mount fixed to the OR table, and a Stryker® Flashpoint 6000 tracking system to track the patient phantom, the tool 110, 20, the display device 100, and the viewpoint. The 3D-printed patient phantom contained segmented anatomy and a corresponding CT volume. During the experiments, surgeons explored the proposed techniques in a predefined order with a think-aloud protocol and no time limit, followed by a semi-structured interview. The surgeons were asked to pay attention to differences in the visualization methods and to consider possible application scenarios. First, surgeons were exposed to use the conventional orthogonal slice visualization controlled by a tracked instrument. Next, the surgeons were presented the novel FVF and SPSV visualization techniques. Thereafter, the surgeons explored the methods with head tracking, namely, the DMVF and VFSV visualization techniques. When using FVF and DMVF, the surgeons were instructed to switch between two modes: segmented 3D structures and direct volume rendering. In the interviews, the surgeons praised the idea to automate slice presentation and to present the images to them that match the orientation of their direct view onto the patient. The overall feedback of the experts on the proposed concept was extremely positive. The surgeons appreciated the fact that for DMVF and VFSV, the surgeons could interact with patient data in a sterile manner, which they considered to be important when an intervention turns out to be more complex than initially expected. The participants agreed that the FVF and SPSV methods could be easily integrated into the established surgical workflow. When asked about possible applications of the proposed concept, the answers included use-cases in complex craniomaxiofacial surgery, and interventions in orthopedics and trauma surgery, and interventions where high precision is utilized, such as endoprosthetics. Finally, the participants agreed that the proposed visualization techniques can help to familiarize with the specific patient anatomy and understand how instruments are currently positioned with respect to a planned trajectory. Participants unanimously agree that the new visualization techniques help with orientation with respect to obtaining an overview of the specific patient anatomy and how the instruments are currently positioned.

What is claimed is:

1. A system for aiding in interaction with a physical object, the system comprising:
   a display device defining a plane and being located on a first side of the physical object; and
   a navigation system coupled to a control system and being configured to:
   register computer images to the physical object;
   track a pose of the physical object and the display device in a common coordinate system; and
   control the display device to render the registered computer images according to the tracked pose of the physical object and the display device; and
   wherein a perspective of the rendering is based on a virtual camera that has a virtual position located on a second side of the physical object opposite to the first side, and wherein the virtual camera has a field-of-view that faces the plane of display device, and wherein the virtual position of the virtual camera updates automatically in response to adjustment to the pose of the display device; and
   wherein the virtual position of the virtual camera is located at a predetermined distance from the plane of display device and wherein the predetermined distance updates automatically.

2. The system of claim 1, wherein the computer images of the physical object are derived from a 3D model, and the control system is configured to control the display device to display one or more slices of the 3D model depending upon the tracked pose of the physical object and the display device.

3. The system of claim 2, wherein the one or more slices are sliced at planes parallel to the plane of the display device.

4. The system of claim 2, wherein the control system is configured to control the display device to automatically change the one or more slices to other slices in response to one or more of the following: the tracked pose of the display device; the tracked pose of the physical object; a tracked pose of a surgical instrument; and a tracked pose of a user's viewpoint.

5. The system of claim 1, wherein the predetermined distance updates automatically in response to at least one or more of the following: the tracked pose of the display device, the tracked pose of the physical object, a tracked pose of a surgical tool; a tracked pose of a user's viewpoint; a type of surgical procedure; and a certain step of a surgical procedure.

6. The system of claim 1, wherein an X-Y placement of the virtual position of the virtual camera relative to the plane of the display device updates automatically in response to at least one or more of the following: the tracked pose of the display device, the tracked pose of the physical object, a tracked pose of a surgical tool; a tracked pose of a user's viewpoint; a type of surgical procedure; and a certain step of a surgical procedure.

7. The system of claim 1, wherein an X-Y placement of the virtual position of the virtual camera relative to the plane of the display device is fixed.

8. The system of claim 1, wherein the pose of the display device is manually adjustable, and the virtual position of the virtual camera updates automatically in response to manual adjustment to the pose of the display device.

9. The system of claim 1, comprising one or more actuators coupled to the display device and the control system being configured to control the one or more actuators to adjust the pose of the display device.

10. The system of claim 9, comprising an input device coupled to the control system and the control system is configured to receive a command from the input device and control the one or more actuators to adjust the pose of the display device in accordance with the command.

11. The system of claim 9, comprising a surgical instrument including one or more trackable features, and wherein the navigation system is configured to track a pose of the surgical instrument in the common coordinate system and control the display device to display an image of the surgical instrument, and wherein the control system is configured to control the one or more actuators to adjust the pose of the display device based on the tracked pose of the surgical instrument.

12. The system of claim 9, comprising a viewpoint tracking system coupled to the navigation system and being configured to track a pose of a user's viewpoint in the common coordinate system and wherein the control system is configured to control the one or more actuators to adjust the pose of the display device based on the tracked pose related to the user's viewpoint.

13. A method of operating a system for aiding in interaction with a physical object, the system comprising a display device defining a plane and being located on a first side of the physical object, and a navigation system coupled to a control system, the method comprising:
   registering computer images to the physical object;
   tracking a pose of the physical object and the display device in a common coordinate system; and controlling the display device to render the registered computer images according to the tracked pose of the physical object and the display device; and wherein a perspective of the rendering is based on a virtual camera having a virtual position located on a second side of the physical object opposite to the first side, and wherein the virtual camera has a field-of-view facing the plane of display device, and automatically updating the virtual position of the virtual camera in response to adjusting the pose of the display device; and wherein the virtual position of the virtual camera is located at a predetermined distance from the plane of display device and wherein the predetermined distance updates automatically.

\* \* \* \* \*